United States Patent
Sliwa et al.

(10) Patent No.: US 9,907,534 B2
(45) Date of Patent: Mar. 6, 2018

(54) SELF-AIMING DIRECTABLE ACOUSTIC TRANSDUCER ASSEMBLY FOR INVASIVE MEDICAL DEVICE APPLICATIONS

(75) Inventors: John W. Sliwa, Los Altos Hills, CA (US); Stephen A. Morse, Menlo Park, CA (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 1532 days.

(21) Appl. No.: 12/638,393

(22) Filed: Dec. 15, 2009

(65) Prior Publication Data

US 2011/0144491 A1    Jun. 16, 2011

(51) Int. Cl.
| | | |
|---|---|---|
| *A61B 8/00* | (2006.01) | |
| *A61B 8/12* | (2006.01) | |
| *A61B 5/00* | (2006.01) | |
| *H04R 17/00* | (2006.01) | |
| *A61B 8/08* | (2006.01) | |
| *A61B 18/14* | (2006.01) | |
| *A61M 37/00* | (2006.01) | |
| *A61B 90/00* | (2016.01) | |

(52) U.S. Cl.
CPC ............. *A61B 8/12* (2013.01); *A61B 5/6885* (2013.01); *A61B 8/085* (2013.01); *A61B 8/429* (2013.01); *A61B 8/4254* (2013.01); *A61B 8/445* (2013.01); *H04R 17/00* (2013.01); *A61B 18/1492* (2013.01); *A61B 2090/378* (2016.02); *A61B 2090/3784* (2016.02); *A61M 37/0092* (2013.01)

(58) Field of Classification Search
CPC ........ A61B 18/1492; A61B 2019/5278; A61B 8/12; A61B 8/445

USPC .... 600/439, 437, 459, 462, 471, 472; 601/2, 601/3; 606/41, 32, 46
See application file for complete search history.

(56) References Cited

U.S. PATENT DOCUMENTS

| | | | |
|---|---|---|---|
| 4,425,017 A | | 1/1984 | Chan |
| 5,630,837 A | * | 5/1997 | Crowley .................... 601/2 |
| 5,646,524 A | | 7/1997 | Gilboa |
| 5,646,525 A | | 7/1997 | Gilboa |
| 5,913,820 A | | 6/1999 | Bladen et al. |
| 6,049,958 A | | 4/2000 | Eberle et al. |

(Continued)

FOREIGN PATENT DOCUMENTS

| | | |
|---|---|---|
| WO | 2004098694 A1 | 11/2004 |
| WO | 2008002654 A2 | 1/2008 |
| WO | 2008107842 A2 | 9/2008 |

*Primary Examiner* — Rajeev Siripurapu
(74) *Attorney, Agent, or Firm* — Dykema Gossett PLLC

(57) ABSTRACT

A directable acoustic transducer assembly is presented for use in a medical insertion device (MID). In an embodiment, the assembly aims an acoustic signal in response to a sensed or detected force or load imposed on the MID. The directable acoustic transducer assembly includes a switch array and a plurality of directional acoustic transducer elements. The switch array responds to the force or load and activates the directional acoustic transducer elements closest to the source of the force or load. The switch array may include a plurality of switches, at least one of which responses to a force or load and may activate directional acoustic transducer elements having a target tissue in the field of view. The assembly includes embodiments that are responsive to various loads. A directable acoustic transducer assembly may be part of a diagnostic and/or therapeutic system, such as an RF ablation system.

21 Claims, 11 Drawing Sheets

(56) References Cited

U.S. PATENT DOCUMENTS

| | | |
|---|---|---|
| 6,233,476 B1 | 5/2001 | Strommer et al. |
| 6,569,160 B1 * | 5/2003 | Goldin et al. .................. 606/41 |
| 6,805,128 B1 * | 10/2004 | Pless et al. ................... 128/898 |
| 7,197,354 B2 | 3/2007 | Sobe |
| 7,220,239 B2 | 5/2007 | Wilson et al. |
| 7,338,486 B2 | 3/2008 | Sliwa et al. |
| 7,343,195 B2 | 3/2008 | Strommer et al. |
| 7,386,339 B2 | 6/2008 | Strommer et al. |
| 7,397,935 B2 | 7/2008 | Kimmel et al. |
| 7,591,816 B2 | 9/2009 | Wang et al. |
| 7,600,410 B2 | 10/2009 | Sliwa, Jr. et al. |
| 2001/0034501 A1 | 10/2001 | Tom |
| 2004/0102769 A1 * | 5/2004 | Schwartz et al. ............... 606/27 |
| 2006/0015096 A1 * | 1/2006 | Hauck et al. ................... 606/41 |
| 2007/0049821 A1 | 3/2007 | Willis |
| 2007/0073154 A1 | 3/2007 | Karasawa |
| 2007/0191829 A1 | 8/2007 | McGee et al. |
| 2007/0191830 A1 | 8/2007 | Crompton et al. |
| 2007/0255276 A1 | 11/2007 | Sliwa, Jr. et al. |
| 2008/0097501 A1 | 4/2008 | Blier |
| 2009/0163909 A1 | 6/2009 | Ma et al. |
| 2010/0168568 A1 | 7/2010 | Sliwa |

\* cited by examiner

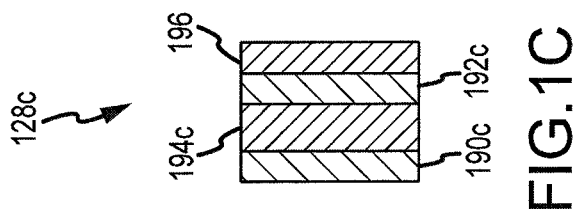
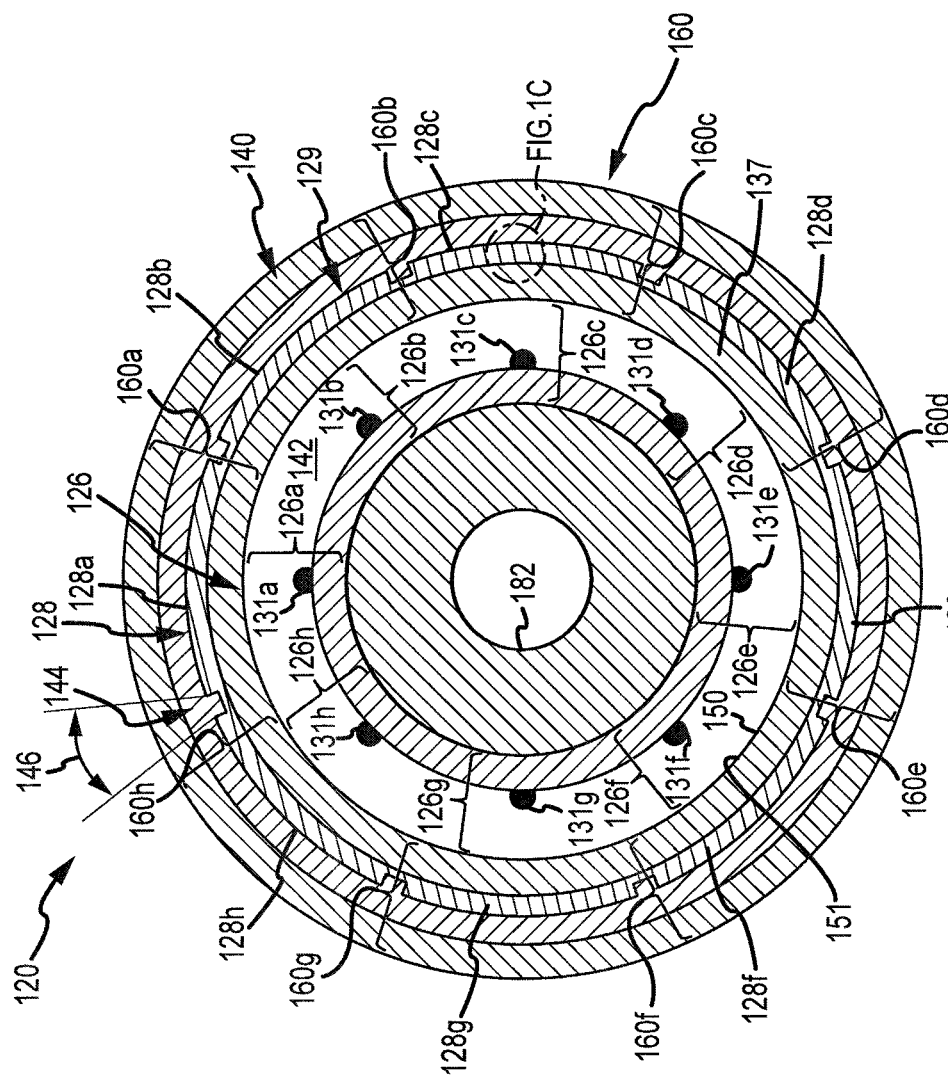

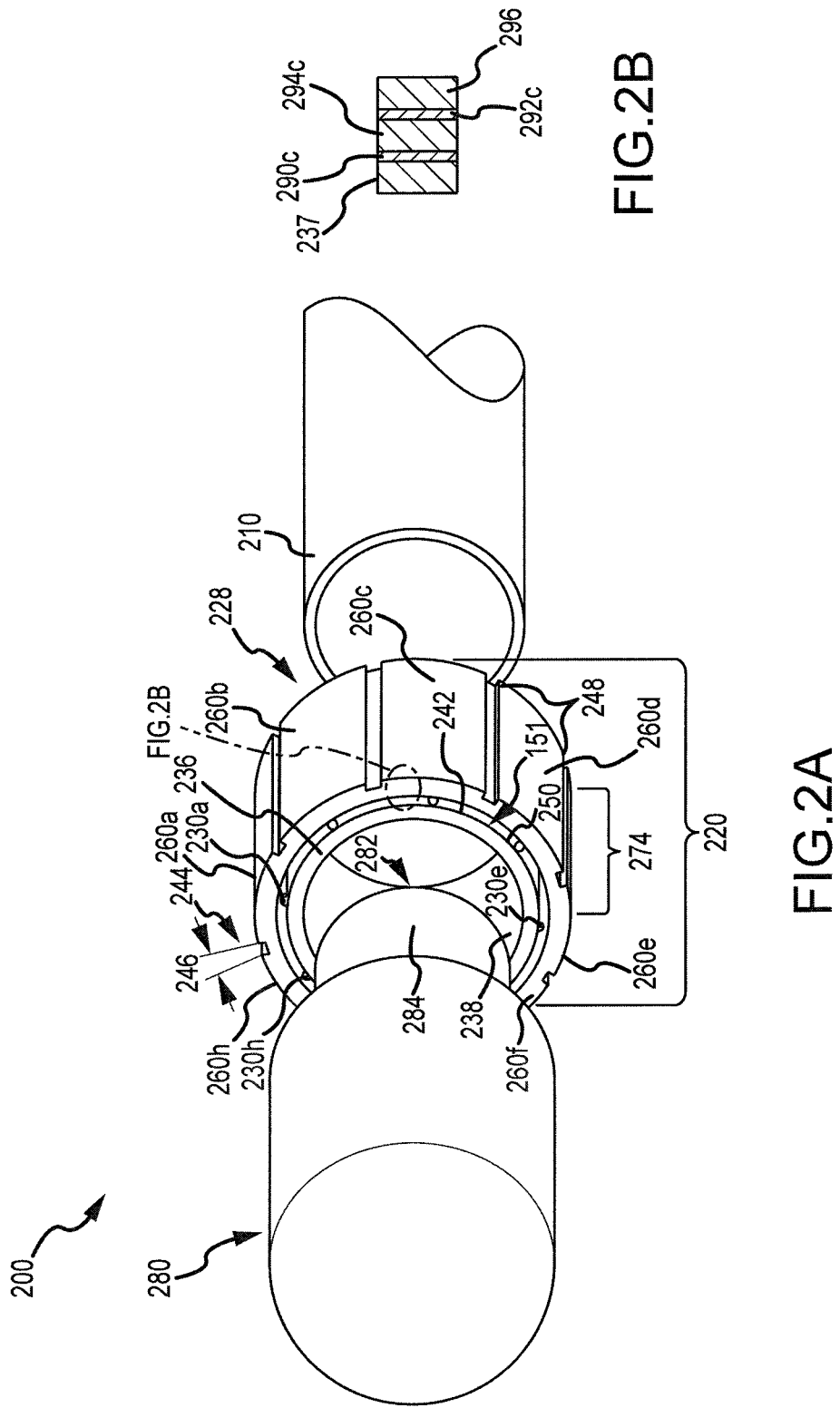

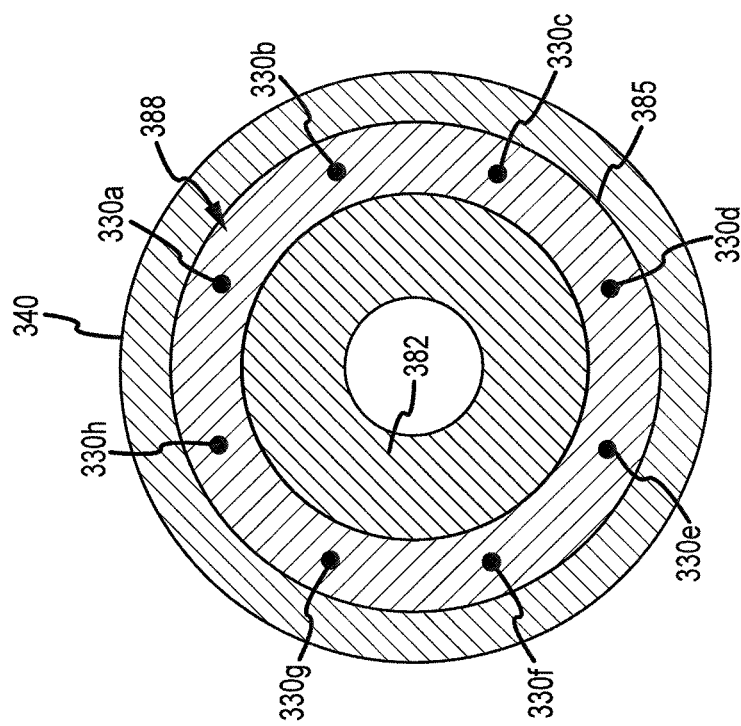
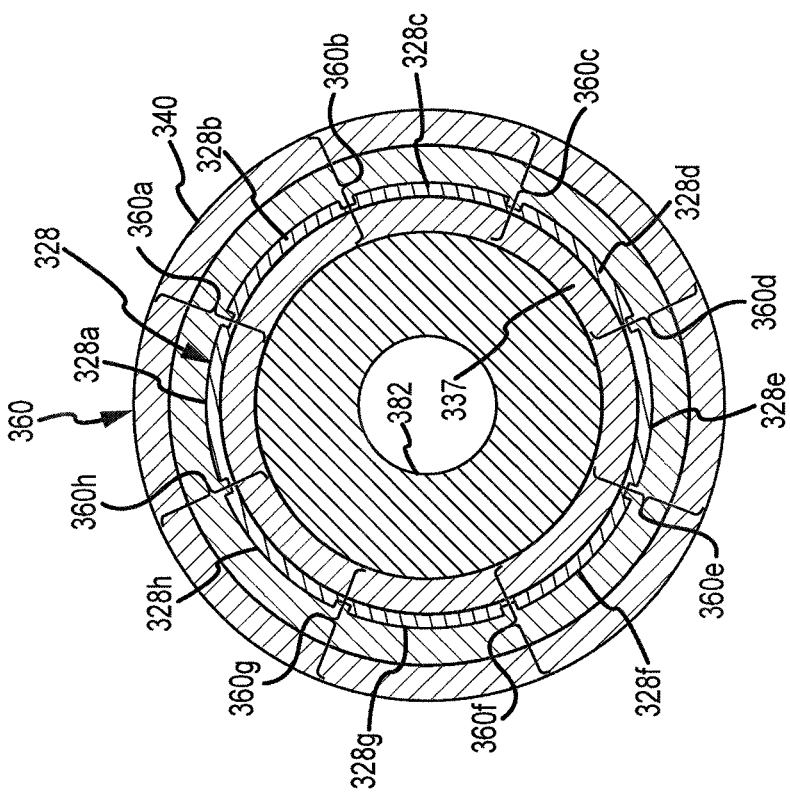

D-D

SELF-AIMING DIRECTABLE ACOUSTIC TRANSDUCER ASSEMBLY FOR INVASIVE MEDICAL DEVICE APPLICATIONS

BACKGROUND OF THE INVENTION a. Field of the Invention

The instant disclosure relates to aiming directional acoustic transducers. Among other things, the disclosure relates to aiming directed acoustic transducers in medical applications.

b. Background Art

Medical insertion devices ("MIDS" or "MID" in the singular) such as, catheters, introducers, sheaths, and scopes are inserted into blood vessels, organs, tissue and other body parts for use in various medical applications. For example, MIDS have been used in therapeutic and diagnostic applications such as, forming of tissue lesions (thermally as with radio-frequency "RF"laser or high intensity focused ultrasound (HIFU)); electrically exciting tissue; electrically sensing voltages and/or currents in tissue; implementing surgical procedures; draining and/or delivering fluid or another flowable medium from and/or to the tissue or organ, respectively; delivering another surgical or medical device or tool; delivering sensors or implants into the tissue; delivering balloon-based therapy; delivering a drug or medicament; and/or monitoring important parameters during medical or surgical procedures.

To diagnose and/or provide therapy to the desired tissue (the "target tissue"), the portion of the MID used in diagnosis and/or the provision of therapy usually needs to be positioned at least proximate to the target tissue, if not in direct contact with the target tissue. With catheters, this tissue contacting or proximate portion which would contain the inventive transducer assembly is generally referred to as the distal end or tip of the catheter. In addition, the MID may need to obtain certain diagnostic or measurement information about the target tissue before, during, and/or after therapy is provided. A variety of ultrasonic transducers have been employed in the pulse-echo or pinging mode for providing the diagnostic or measurement capability from a catheter tip. The emitted and received acoustical waves of such transducers are either directed or nondirected (omnidirectional) at angles to the long catheter axis or the more-rigid tip axis. Directed transducers emit/receive along one or more angular directions relative to a line typically perpendicular or at a small angle to the catheter tip axis. Directed transducers include fixed (relative to catheter) mechanically focused transducers, mechanically steerable rotating (relative to catheter) mechanically focused transducers, and fixed (relative to catheter) electronically steerable phased array 2D and 3D imaging transducers. The directions at given times are known, and thus the acoustic reflection data received is known to be that along one or more specific (scan) lines or directions penetrating the adjacent tissue. Directed transducers may provide image information along each such directed (scan) line or direction.

Nondirected transducers are typically omnidirectional, meaning they simultaneously (as opposed to serially) emit/receive at all angles throughout all or most of 360 degrees of arc about the catheter tip axis, all such angles typically being orthogonal or nearly orthogonal to the catheter tip axis. Typically the transducer is cylindrical with its cylindrical axis arranged along the catheter tip axis, and it emits/receives from its 360 degree cylindrical external surface substantially generally orthogonal to the common cylindrical transducer and tip axis. Because the acoustic reflection data received by an omnidirectional transducer comes from all angular or rotational directions simultaneously and is inevitably electronically summed before analysis or presentation, it is unknown which reflections or how much of a given reflection at a certain radial depth (an echo time-delay amount) comes from a particular angular direction. Nondirected or omnidirectional transducers do not provide an image, partial image, or image information. However, construction is relatively simple and the total reflected power from each radial distance summed from all angles may be known.

Directed and omnidirectional transducers emit acoustic or ultrasonic pulses along one or more directions and then listen for resulting echoes or reflections coming from various tissue depths from those one or more directions. Such echoes or reflections come from internal tissue interfaces, blood vessels, natural lesions and tumors, and from ablated lesions having ablation-induced microbubbles or acoustic impedance differences. Since the acoustic velocity in natural tissue is known (i.e., about 1540 meters/sec with very little variation), the distance or depth to a tissue reflector can be determined knowing its echo delay time and dividing that time by a factor of two since the acoustic waves undergo a two-way round trip. The thickness of a tissue layer or blood chamber may be measured by looking at the difference between the depths or distances of its frontside and backside reflections or echoes.

A reflector depth or distance along a single direction for an omnidirectional transducer cannot be determined because the omnidirectional transducer is essentially simultaneously measuring all directions at once and adding the received signals. The signal-to-noise (S/N) of directed transducers is superior to an omnidirectional transducer both because directed transducers are looking only at the target and because all the energy that would have been involved with a 360 degree omnidirectional transducer is instead restricted to a small angle of the directed beam such that all the energy is injected and received along the specific direction(s) of interest (i.e., the energy efficiency is better).

Directed and omnidirectional transducers are typically operated in the frequency range of 2 MHz to 20 Mhz. The higher end of these frequencies provides less penetration but more axial depth resolution, so the higher frequencies are used for the highest possible accuracy in thin or shallow tissues. A piezotransducer transmit pulse, typically of tens of volts in amplitude, will contain one or a few sinusoidal waveforms at the above center frequency. The received echoes typically include those from a number of buried interfaces at various depths plus one or more reverberations (e.g., false reflections) coming from the transducer itself as is well known to the art. Emitting pulse lengths and echo delay times are typically measured in microseconds or less for 1 MHz and above ultrasound as is known in the echo arts.

BRIEF SUMMARY OF THE INVENTION

There remains a need for an omnidirectional, pinging capable (pulse echo distance sensing or lesion detection) product that does not utilize mechanically rotated transducers and/or electronically steered phased array transducers. It will be appreciated that mechanically rotated transducers and/or electronically steered phased array transducers involve substantial additional complexity and cost relative to a single tubular omnidirectional transducer element which does not move or rotate relative to the catheter tip or body and does not utilize phase-delay circuitry.

As described in the present disclosure, a populated ring of transducers in the form of a selectively electrically directable transducer assembly having available transducer elements distributed around the 360 degrees field of view from the catheter tip, wherein only one or a few transducer elements which are detected as usefully facing a target tissue may be operated, and wherein all other transducer elements on the ring may be turned off, may be useful. A "ring" of transducers or transducer elements means at least two, as many as 128 or greater, and most typically in the range of 5 to 24. The transducer elements may be generally equally spaced circumferentially around the 360 degrees. Thus, a physician or physiologist using an inventive MID (e.g., an RF catheter with the interrogating or imaging transducer ring) to perform a therapeutic function, such as RF thermal ablation, does not need to realign the MID (rotate the catheter tip) with the target tissue each time he/she wishes to measure tissue thickness and/or assess a lesion created or being created by the ablation procedure. The probe tip itself switches on the tissue-facing transducer elements via the tip loading caused by the contacting tissue. The inventive MID thus comprises an "omnidirectional" ring or tube transducer that is configured for only certain (e.g., properly directed) portions to be operated at a given time. The inventive MID is "omnidirectional" in the sense that it is configured for emitting/receiving acoustical waves in all directions, but no longer at all angles and/or directions simultaneously. In an embodiment, an electrically self-directed transducer assembly comprising several ring-mounted transducers advises an omnidirectional ablative therapy. The self-directed individual or subtransducers are arranged to emit/receive only along a known direction (e.g., the direction toward the tissue of interest). The RF tip ablating action itself is known to inherently burn only the contacted tissue and not the blood on the opposite tip face because the tissue-tip contact portion offers more favorable RF-impedance coupling. This acoustic measurement or monitoring direction may comprise anywhere from a few degrees to a few tens of degrees (e.g., about 1 degree to about 30 degrees) and within this angular arc, in the simplest embodiment, all reflections received at given times (distances) are summed regardless of angle-of-arrival. It will be appreciated that the subgroup of usefully-directed operated transducer elements can be caused to ping at a 90 degree angle to the tip circumference (i.e., generally straight out) or can be caused to ping at an angle with a somewhat different known set of element phase delays. In fact, if the subgroup is fired at multiple such angles to produce multiple scanlines, then a user is actually imaging, however, in a novel manner wherein the rest of the array not usefully directed is turned off by the inventive tip motion-based mechanical switching feature. Accordingly, at one extreme, one or a few elements create a single orthogonal scanline, whereas at the other extreme, a group of elements produce multiple steered scanlines comprising an image portion. It is anticipated that the most economical embodiments will avoid the use of transducer element firing phase delays, and therefore, fire just one or two closely spaced usefully directed transducer elements at a given time (without phase delays) to obtain an orthogonal pinged echo. Herein, the term "scanline" means a direction along which one or more echoes are received-regardless of whether the "scanline" is formed by one or more individually, simultaneously, or phase-coordinated firing transducer elements.

In accordance with an embodiment, the directable acoustic transducer assembly may include a plurality of generally radially directional acoustic transducer elements and an electrically coupled electromechanical switch array. The electromechanical switch array may be configured to activate the appropriate directional acoustic transducer element(s) in response to a tissue contact load imposed on the MID and/or on the directable acoustic transducer assembly. When activated by the switch array, the directional acoustic transducer elements may be configured to aim (e.g., activate) an acoustic pinging beam in the approximate direction of the tissue causing the tip loading (i.e., toward the target tissue) and likewise receive the reflected echoes from various depths along that direction. It will be appreciated that a given bending load on the catheter tip will bend the tip in a certain direction, and that the electrical switches in the switch array can be arranged such that the ones which are closed upon the specific bending event are the ones that switch the transducer elements facing the tissue on. Typically, the switches closed by such a bending event will be about 180 degrees opposite the contacting tissue, as that opposed side of the tip is in compression due to the bending.

A MID, such as a catheter, introducer, sheath, and/or scope, in which an inventive directable acoustic transducer assembly is implemented, generally includes an elongated body and a distal tip. The electrically self-directable (e.g., self-activatable) acoustic transducer assembly may be connected with the body and the tip and detect the direction of a tissue load on the tip and/or directable acoustic transducer assembly and, in response, aim (e.g., selectively activate) a directional acoustic signal in the direction of the tissue causing the load by switching that transducer subset on. In other words, the catheter tip senses mechanically, via its loading and bending or distortion, which face of the distal tip is being pushed or loaded by the contacting tissue and is wired during manufacture such that the transducer elements on the tissue-contacting face will be activated or closed.

In general, the inventive directable acoustic transducer assembly may include an electromechanical switch array and a plurality of generally radially directed acoustic transducer elements mounted around a 360 degree ring wrapping around the catheter tip. The electromechanical switch array may further include a plurality of switches or contact pairs. At least one of the switches or contact pairs may be (preferably) closed or opened in physical response to a load caused by the contacting target tissue and may activate one or more directional acoustic transducer elements having that target tissue in their field of view. Moreover, the disclosed directable acoustic transducer assembly may include embodiments that respond to tissue loads that cause translational movement in the directable acoustic transducer assembly, angulating movement in the tip of the MID, and/or tip movement along the longitudinal axis of the tip. In each of these embodiments, the switches may be in communication with the directional acoustic transducer elements so that when a switch is closed (or, alternatively, opened) in response to a load, the directional acoustic transducer element nearest to the tissue causing the load is activated or connected. In general the transducer element(s) which are electromechanically turned on will form a collective acoustic beam as they are all fired and as they then listen for echoes. The fired elements may also use an acoustic lens or utilize phase delays applied across the active elements to further form or steer the beam in transmit and/or receive modes. The phase delays, if utilized, may be fixed phased delays to dramatically reduce cost relative to that of a true phased array imaging device having real time computed variable phase delays. As described herein, the most cost effective embodiments avoid the use of phase delays or at least use a fixed set of phase delays which can be implemented in a fixed circuit.

A directable (e.g., self-directed or self-activated) acoustic transducer assembly as disclosed may be part of a system used to deliver diagnostic and/or therapeutic procedures to a target tissue. For example, a directable acoustic transducer and associated pulser and echo receiving circuitry may be used in connection with an RF ablation catheter system in a physically cointegrated manner (i.e. the ablation tool tip has a self-directing acoustic pulse-echo capability). Such a system may include a user interface, RF catheter, RF catheter manipulator and an ablation controller. The system likely also includes an ablation RF power supply. The RF catheter may include one or more magnetic sensors or electrical spatial tracking electrodes, a directional acoustic transducer assembly, and an RF ablation tip assembly. The user interface, spatial tracking electrode (or tracking magnetic sensor) and RF catheter manipulator can be employed to controllably move the catheter within the anatomy and track the position/orientation of the catheter tip. The directional acoustic transducer assembly may be used to gather information about the target tissue before, during or after ablation in the case of an ablation application of the invention. The self-directed acoustic transducer assembly may be configured to respond to a load imposed on it by a contacting target tissue, thereby aiming (i.e., selectively activating) the acoustic pulse and echo beams of tissue-adjacent (or usefully tissue-facing) transducer elements in the direction of the target tissue. A user or practitioner may automatically be provided with his/her acoustic feedback from the appropriate tissue target regardless of what state of rotation (e.g., about the tip axis) the catheter tip is at when it contacts tissue because the tissue-facing transducers may always be turned on regardless of the rotational orientation of the catheter tip/body upon tissue contact. In accordance with another embodiment of the invention, the user articulates (e.g., bends) the catheter tip relative to its body or lumen, and that user action itself activates the electromechanical switching features. In that case, the user will typically have the catheter tip on fluoroscopy and can predetermine which direction the tip needs to be bent before tissue contact. This approach has the advantage that the user can apply higher loads more safely to the tip than the tissue safely can (e.g., with tip-bending steering wires). Regardless of whether the tissue loading causes the switching or user loading causes the switching (before and/or during tissue contact), the electromechanical switch array is selectively angularly deformed closed by those forces.

The invention may be configured to provide a transducer catheter-tip pinging capability which offers directional benefits, but avoids the added cost, complexity and reliability risks of mechanically rotating or multielement electronically-switched phased (e.g., steered) arrays. The directional benefit (versus nondirectional disadvantage) is that the user knows angularly where in space relative to the pinging tip a given tissue reflector is situated. An embodiment of the invention has a ring of radial-looking transducers of which only the appropriate ones facing the tissue target are turned on to ping that tissue while all others remain off. The invention may be considered omnidirectional, but with self-switchable angular sections that electromechanically make it directional in a desired direction at a given moment. This turning on and off of a subgroup of transducer elements pointing in the direction of interest may be transparent to the catheter user and may automatically adapt to which face of the catheter tip happens to rest upon the target tissue. Presuming the catheter therapy itself, such as RF ablation, is omnidirectional in nature (i.e. ablation proceeds the same way regardless of the rotational orientation of the tip along its axis as it is put in tissue contact) then the practitioner thereby need not concern himself/herself whatsoever about the axial and/or rotational orientation of the catheter tip relative to the tissue. RF ablation will ablate the contacting tissue and the electrically selected appropriate subset of radial transducers will image or interrogate the lesion region. "Omnidirectional" with respect to RF catheter therapy or ablating means that the particular rotational angle the ablating tip is placed at against tissue is inconsequential. It forms the same lesion preferably (due to better electrical tissue coupling versus blood coupling) at its tissue-contacting surface. RF ablation is known to act in such an advantageous manner.

The foregoing and other aspects, features, details, utilities, and advantages of the present invention will be apparent from reading the following description and claims, and from reviewing the accompanying drawings.

BRIEF DESCRIPTION OF THE DRAWINGS

The disclosure can be better understood with reference to the following drawings and description. The components in the Figures are not necessarily to scale, emphasis instead being placed upon illustrating the principles of the invention.

FIG. 1B depicts a cross-sectional view of the directable acoustic transducer assembly of FIG. 1A taken along line A-A;

FIG. 1C depicts a partial cross-sectional view of a transducer of the directable acoustic transducer assembly of FIG. 1B;

FIG. 2A depicts an exploded isometric view of a further embodiment of a directable acoustic transducer assembly implemented with a medical insertion device;

FIG. 2B depicts a partial cross-sectional view of a directional acoustic transducer element of the directable acoustic transducer assembly of FIG. 2A.

FIG. 3B depicts a cross-sectional view of the directable acoustic transducer assembly of FIG. 3A taken along line B-B;

FIG. 3C depicts a cross-sectional view of the directable acoustic transducer assembly of FIG. 3A taken along line C-C;

DETAILED DESCRIPTION OF THE INVENTION

Figure 1A:
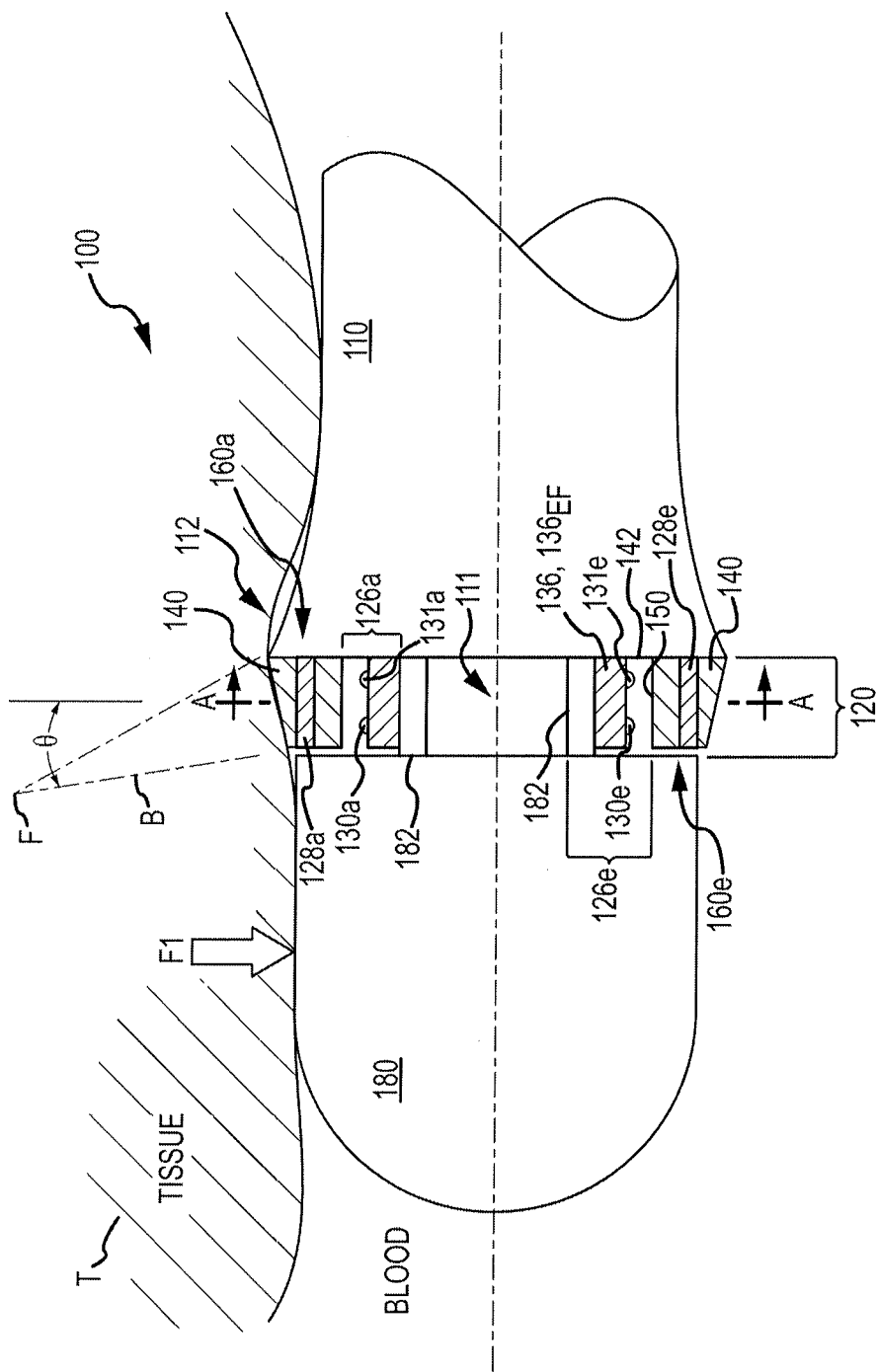
FIG. 1A depicts a partial cross-sectional view of a directable acoustic transducer assembly implemented with a medical insertion device.

FIG. 1A generally depicts a self-directed acoustic transducer assembly 120 as implemented in connection with a MID 100. In the illustrated example, the MID 100 is a catheter and generally includes a body 110 and tip 180. The tip 180 may include a flexible boss 182 that facilitates or enables the connection of tip 180 with the body 110. Although generally shown implemented in connection with a catheter, the directable acoustic transducer assembly 120 and all other embodiments disclosed herein may be implemented in connection with a variety of MIDS, including without limitation, various sheaths, introducers, and scopes.

Referring to FIGS. 1A and 1B, the illustrated embodiment of a directable acoustic transducer assembly 120 includes a circumferential or circular switch array 126 and at least one directional acoustic transducer 160 (e.g., a set of circumferentially distributed selectively directable acoustic transducers 160). The selectively directable acoustic transducer 160 includes a plurality of directional acoustic transducer elements 160a, 160b, 160c, 160d, 160e, 160f, 160g, 160h which respectively include transducers 128a, 128b, 128c, 128d, 128e, 128f, 128g, 128h, and further respectively include an underlying acoustic backing layer 137 and an overlying acoustic lens 140. The acoustically attenuative backing layer 137 is connected and/or integrated with the transducers 128a-128h and may also provide mechanical support. The backing layer 137 may also include or provide a controlled acoustic impedance and/or controlled acoustic attenuation to minimize acoustic ringdown or reduce backward propagated losses in the known manner.

The transducers 128a-128h typically include hot and ground electrodes with the piezoelectric material sandwiched in-between, such as a piezoceramic, composite piezoceramic and/or piezopolymer piezoelectric material. Alternately, the transducers 128a-128h may include one or more CMUTs (Capacitive Micromechanical Ultrasound Transducers), electrostatic-based transducer elements, magnetostrictive elements, thermoacoustic elements and/or photoacoustic elements. For example, without limitation and as generally illustrated in FIG. 1C, transducer 128c may include an inner (e.g., hot) electrode 190c, a piezoelectric material 194c and an outer (e.g., ground) electrode 192c. Although each of the transducers 128a-128h may be formed separately, as illustrated in this embodiment, the transducers 128a-128h can more preferably be formed out of an initially monolithic transducer ring 128, for example, by laser-dicing or etching the monolithic ring 128 and/or associated electrodes. The transducers 128a-128h may also be formed in the general shape of a cylinder. Although the transducers 128a-128h are described as formed in a ring or cylinder, the transducers 128a-128h may be formed in any number of other various shapes in accordance with other embodiments of the invention. The transducers 128a-128h may also include an overlying acoustic matching layer 196 that provides compensation for the difference between the acoustic impedance of the transducers 128a-128h piezomaterial and the acoustic impedance of the tissue being examined. The transducer ring 128 may generally comprise an acoustic backing layer 137, which is rigidly bonded to a piezomaterial, an acoustic matching layer 196, and an acoustic lens 140, which are all bonded together. The piezomaterial preferably has a thin, electrically conductive frontside and backside electrode coating. The acoustic lens 140 faces the tissue target and steers or forms the acoustic beam.

As shown in connection with directional acoustic transducer element 160c which includes the transducer 128c, the matching layer 196 may be connected with the outer electrode 192c and the lens 140. A similar or essentially identical configuration may be employed in connection with the other directional acoustic transducer elements 160a, 160b, 160d-160h.

For a transducer, such as transducer 128c, to produce an acoustic transmit signal, a pulsed voltage is generally applied across the inner electrode 190c and outer electrode 192c. The resulting emitted acoustic signal propagates through the matching layer 196 to be transmitted outwards from the MID 100 through the lens 140. In an embodiment, the lens 140 may be configured to form an angle of preferably about 20 degrees to about 50 degrees with respect to the longitudinal axis 111 of the directable acoustic transducer assembly 120. As a result, the acoustic signal is deflected by the lens 140 from a path that is approximately perpendicular to the longitudinal axis 111 of the directable acoustic transducer assembly 120, to a path that is angled towards the tip 180 of the MID 100. For example, referring to FIG. 1A, the transducer tip 180 may contact tissue T such that the contacted tissue exerts a reaction force F1 upon the tip 180. This force may cause the relative motion or angulation of the tip 180 relative to the body 110, thereby closing one or more switches on the switch array 126, which turn on one or more appropriate transducers 128a-128h facing the tissue T which in turn create an acoustic beam B. Acoustic beam B may be tilted forward or distally at an angle θ toward the catheter tip because of the acoustic lens 140. This may help assure that the beam B penetrates the tissue region being ablated by the adjacent RF ablator tip 180. As shown in FIG. 1A, RF ablator tip 180 may be positioned distally of directable acoustic transducer assembly 120. Typically the transducer ring 128 diameter will be between about 2 and 6 mm with a common size around 2.0-3.5 mm. The transducer 128a-128h width (measured along the catheter axis) may typically be in the range of about 0.5-3.0 mm. The transducer frequency may typically be in the range of about 7-25 MHz with about 7-12 MHz being more common to attain significant few centimeter penetration and reasonable range resolution. The transducer ring 128 may typically be formed from a monolithic piezotube. A user may at least laser etch or scribe the hot electrode 190c to create electrically selectable ring regions, but more beneficially may also actually physically cut the ring piezomaterial between each subtransducer such that acoustic crosstalk between the separated transducers is minimized.

To take acoustic measurements or otherwise gather information from or about tissue with the inventive self-directable acoustic transducer assembly 120 implemented with the MID 100, one or more of the directional acoustic transducer elements 160a-160h facing the target tissue are to be activated. In other words, the directional acoustic transducer element(s) 160a-160h with a field of view shown by the beam B of FIG. 1A that encompasses the target tissue of interest is/are selectively activated, such as by force F1. A directional acoustic transducer element, such as 160c, may be activated when a voltage is applied across the electrodes 190c, 192c of the corresponding transducer 128c. The voltage application is enabled or caused by the forceful closure of one or more contacts in the circumferential or circular switch array 126. An advantage of the self-directed transducer ring 128 is that a tissue contact load causes the structure to deform such that one or more of the favorably directed transducer electrical contacts on the switch array 126 are closed and the connected transducers are activated during the tip-loaded period. This simply requires that the adjacent halves of the circumferential or circular switch array 126 be arranged to move relative to each other. To do this, one or both halves of the circumferential or circular switch array 126 may be moved relative to the other. The halves of the circumferential or circular electromechanical switch array 126 may preferably close (or less preferably open) one or more switches upon loading of the tip. This event, therefore, now electrically connects one or more transducer elements 160a-160h, such that it or they can be electrically driven to transmit and receive. The actual pulsing-related switching may likely still be completed in a supporting console. Thus, the electromechanical switching always at least provides an operative or closed circuit for one or more transducer elements 160a-160h which can then be driven or coupled into in transmit and receive modes. In a preferred approach, the system drives whichever transducer elements 160a-160h are connected by the mechanical closure of the electromechanical switch(es).

To selectively activate the directional acoustic transducer elements 160a-160h so as to place the target tissue in the field of view of at least one of the elements 160a-160h, a circumferential or circular switch array 126 may be employed to selectively connect and supply a pulsing voltage to the appropriate acoustic transducer elements 160a-160h and then to passively receive the returning echoes. The switch array 126 includes a plurality of switches 126a, 126b, 126c, 126c, 126d, 126e, 126f, 126g, 126h. "Switch" means any element whose distortion or mechanical loading causes it to usefully change conductance, such as from electrically open to electrically closed or from a high resistance or impedance to a low resistance or impedance. The simplest possible such switch element is a mechanical electrical contact wherein a first contact, such as the depicted contact-bump, comes into physical contact with a second opposed mating contact or contact surface. The contact-bump typically comprises a metallic material such as gold or gold plated copper. In the illustrated embodiment, the switches 126-126h include a plurality of first contacts proximal to the body 110 ("proximal first contacts") 131a, 131b, 131c, 131d, 131e, 131d, 131e, 131f, 131g, 131h, a plurality of first contacts distal from the body 110 ("distal first contacts") 130a, 130b, 130c, 130d, 130e, 130d, 130e, 130f, 130g, 130h (only 130a and 130e are shown) and a second contact 150. The switches 126a, 126b, 126c, 126c, 126d, 126e, 126f, 126g, 126h may be closed when the proximal first contacts 131a, 131b, 131c, 131d, 131e, 131d, 131e, 131f, 131g, 131h, respectively, and/or the distal first contacts 130a, 130b, 130c, 130d, 130e, 130d, 130e, 130f, 130g, 130h, respectively, come into electrical communication with the second contact 150. For example, switch 126a may close if (a) the proximal first contact 131a comes into electrical communication with the second contact 150; (b) the distal first contact 130a comes into electrical communication with the second contact 150; or (c) both the proximal and distal first contacts 130a, 131b, respectively, come into electrical communication with the second contact 150.

The proximal first contacts 131a-131h and the distal first contacts 130a-130h may be generally, respectively, aligned with each other along the longitudinal axis 111 of the directable acoustic transducer assembly 120. The directable acoustic transducer assembly also includes a support 136, to which the distal and proximal first contacts 130a-130h and 131a-131h, respectively, are mounted. The support 136 may be connected with the boss 182 of the tip 180 and is generally comprised of a non-electrically conductive material, such as alumina, glass, polyimide or pc-board material. In an embodiment, the distal and proximal first contacts 130a-130h, 131a-131h, respectively, and the support 136 may be formed in the shape of a ring 129. The support 136 may also be formed in, for example and without limitation, any polygonal or cylindrical shape. Although these shapes are described in detail, the support 136 may comprise any number of other various shapes in accordance with other embodiments of the invention. Such a ring 129 may, for example and without limitation, be manufactured using a variety of thin film, hybrid and/or flex circuit technologies and/or wafer-bumping technologies. The ring 129 may further comprise ceramic substrates and electrical interconnects (e.g., multilayer internal interconnections and vias) configured for connection to directional acoustic transducer elements 160a-160h. Thus, the distal and proximal first contacts 130a-130h, 131a-131h, respectively, and support 136 are subject to mass production and/or batch fabrication in panel form, which can provide a large manufacturing efficiency and/or cost benefit given their tiny size. In accordance with an embodiment of the invention, the transducer elements 160a-160h may be fabricated upon one or both halves of the circumferential or circular switch array 126. In accordance with another embodiment of the invention, the transducer elements 160a-160h may be separately fabricated from the circumferential or circular switch array 126.

The second contact 150 may be connected to an inner surface 151 of the directable acoustic transducer assembly 120, such as by electroless plating, electroplating, lamination and etch-definition or physical vapor deposition, and may be separated from the distal first contacts 130a-130h and/or proximal first contacts 131a-131h by a gap 142. The gap width is determined by the amount the gap closes when the tip is bent within its operational bending range under the influence of force F. For example, for a tip diameter D and therefore, a tip radius R of D/2, and a maximum tip bending angle a (e.g., chosen to be between about 15-40 degrees), the gap width G which would be closed can be determined in accordance with the following calculation: $G = R \times \tan(\alpha)$. The gap 142 may be filled adjacent and laterally between the contacts (e.g., between second contact 150 and distal first contacts 130a-130h and/or proximal first contacts 131a-131h) with an elastomeric compressible, hydrophobic material, such as a ePTFE (polytetraflouroethylene) film or layer, to prevent fluids such as, blood or water, from penetrating into the gap 142. However, the gap 142 may not be filled so as to interfere with closure. Thus, this elastic hydrophobic material keeps blood out yet still allows for direct-contact mating contact closure. Although, in FIG. 1B, second contact 150 is shown to be a single, continuous contact that is common to the proximal and distal first contacts 131a-131h, 130a-130h, respectively, the second contact 150 may include a plurality of contacts that each correspond to one of the distal and proximal first contacts 130a-130h, 131a-131h, respectively, or to pairs of distal and proximal first contacts, 130a-131a, 130b-131b, 130c-131c, 130d-131d, 130e-131d, 130e-131e, 130f-131f, 130g-131g, 130g-131g. Tip articulation causes a gap change, and the gap change closes (or less preferably opens) one or more contact pairs 130a-130h, 131a-131h, 150. The closing contact(s) enable pinging emission and/or echo-reception from one or more transducer elements 160a-160h on the ring 128. The wiring of contacts 130a-130h, 131a-131h, 150 to transducers 128a-128h within the ring 128 is typically such that closure of a tissue opposite contact will enable a tissue proximal transducer, as closure of that contact indicates tissue contact on the opposite face. In a "gap closure event," the one or more contacts, may close simultaneously or may close sequentially with ever increasing tip articulation depending on design. Progressive contact closures can be easily arranged for by providing some elastic foundation (such as elastic foundation $136_{EF}$ in FIG. 1A) or mounting for one of both mating contact support surfaces (i.e., the contacts themselves could also be situated upon underlying elastic or bendable foundations which are a layer of or comprise the contact ring substrates). In accordance with an embodiment of the invention, the system or user may relate the increasing number of closed switches to the tissue-contact force (i.e., the electromechanical switch array thereby also gives an indication of applied-force in at least a few magnitude steps). The number of directional acoustic transducer elements 160a-160h activated by the switch array 126 may correspond to the load on the medical insertion device. For example, a greater load on the medical insertion device 100 may activate a greater number of directional acoustic transducer elements 160a-160h than a smaller load. Similarly, the number of activated directional acoustic transducer elements 160a-160h may indicate the load magnitude and/or tissue contact force. The number of directional acoustic transducer elements 160a-160h activated by the switch array 126 may be subject to a maximum design limit (e.g., one to five directional acoustic transducer elements) in accordance with an embodiment of the invention. In the typical case, whatever number of transducer elements 160a-160h are enabled will be physically centered on the tissue contact region. The stiffness and thickness of the elastomer can be chosen to determine the bending angle required to close a given number of contacts.

In an embodiment, there is at least one switch 126a-126h associated with each directional acoustic transducer element 160a-160h. Generally, this provides at least one first contact (distal first contact 130a-130h or proximal first contact 131a-131h) for each directional acoustic transducer element 160a-160h. In the example shown in FIGS. 1A and 1B, the directable acoustic transducer assembly 120 includes eight switches 126a-126h and eight directional acoustic transducer elements 160a-160h. In addition, each switch 126a-126h include a distal first contact 130a-130h, respectively, a proximal first contact 131a-131h, respectively, and share the second contact 150. However, the number of these elements is shown for exemplary purposes only and there may be almost any number of switches, contacts, and/or directional acoustic transducer elements. The number of "on" transducer elements 160a-160h may be restricted to the angular tissue contact region (or somewhat narrower region), meaning that the axial included angle of the "on" transducer elements 160a-160h will typically be 120 degrees (out of 360 degrees) or less, and more preferably in the range of 10-100 degrees, and most preferably in the range of 10-90 degrees. This may typically include from one to five "on" transducer elements depending on how many such elements are provided. Although one to five "on" transducer elements are mentioned in detail, there may be more "on" transducer elements in various embodiments of the invention. This allows for designs wherein the full lesion width is monitored or just a central lesion portion is monitored. In accordance with an embodiment of the invention, there will always be at least one directional acoustic transducer element 160a-160h activated when the tip 180 reaches a minimum deformation.

The contact switches 126a-126h may be provided in electrical communication with the directional acoustic transducer elements 160a-160h so that when a load F1 (or a vector component of a load) approximately perpendicular to the longitudinal axis 111 is placed on the tip 180 of the MID 100 by, for example tissue, one or more of the switches 126a-126h which are located on the MID 100 generally opposite the force or load F1 electrically activate one or more of the directional acoustic transducer elements 160a-160h that face the tissue causing the force or load. The one or more of the switches 126a-126h may be provided in electrical communication with the opposite directional acoustic transducer elements 160e, 160f, 160g, 160h, 160a, 160b, 160c, 160e, respectively via electrical traces and/or other electrical interconnections. Thus, the self-directable acoustic transducer assembly 120 can be configured to self-identify the direction of the sensed or detected force or load and self-activate or enable the one or more directional acoustic transducer elements (e.g., elements 160a-160h) that have the source of the force or load (e.g., tissue causing a load) within their field of view. In other words, the self-directed acoustic transducer assembly 120 can be configured to be substantially and preferably "self-aiming."

Figure 5A:
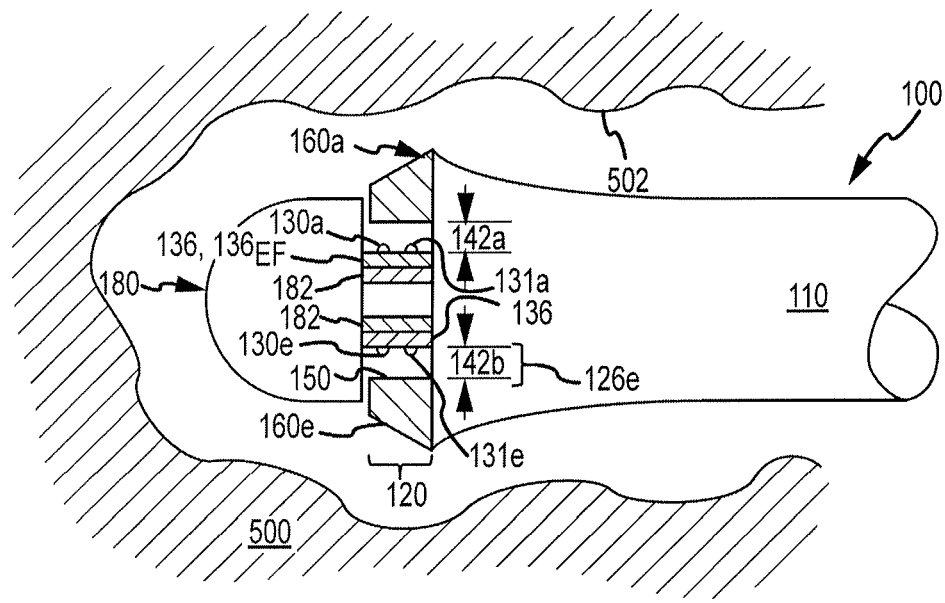
FIG. 5A depicts a partial cross-sectional view of the directable acoustic transducer assembly implemented with the medical insertion device of FIG. 1 inserted into tissue.
Figure 5B:
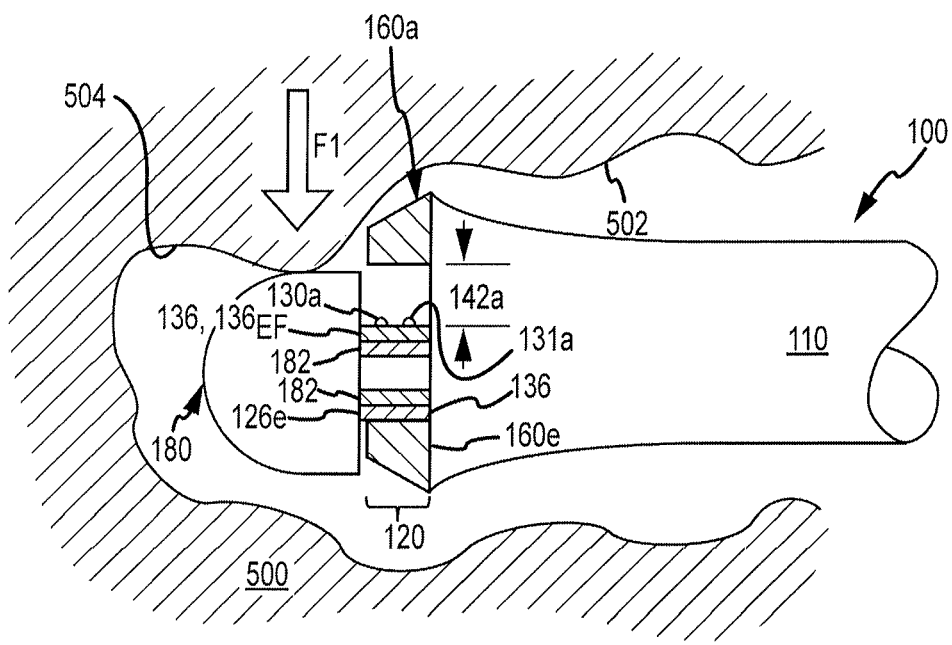
FIG. 5B depicts a partial cross-sectional view of the directable acoustic transducer assembly implemented with the medical insertion device of FIG. 1 inserted into tissue that applies a translational load to the assembly.

An example of the way in which a lateral tissue load selectively activates the directable acoustic transducer assembly 120 is shown in FIGS. 5A and 5B. In FIG. 5A, the MID 100 has been inserted into tissue 500, but does not contact the tissue wall 502. The tip 180 and boss 182 are generally coaxial with the directionable acoustic transducer assembly 120, and the gap 142a between the distal and proximal first contacts 130a, 131a and the second contact 150, and the gap 142b between the distal and proximal first contacts 130e, 131e and the second contact 150, are about equal. The switches 126a, 126b, 126c, 126d, 126e, 126f, 126h are in communication with the opposing directional acoustic transducer elements 160e, 160f, 160g, 160h, 160a, 160b, 160c, 160d, respectively. Thus, switch 126e is in communication with directional acoustic transducer element 160a so that when switch 126e closes, a transmit and receive voltage waveform is applied and received across the contacts of directional acoustic transducer element 160a.

In the example shown in FIG. 5B, the tip 180 comes into contact with a bump 504 in the tissue wall 502 such that a lateral load is placed on the tip 180. The tissue load F1 causes a translational motion in the tip 180 and boss 182 in the direction of the tissue load F1. Due to the load, the flexibility of the boss 182 and the compressibility of the ePTFE or other deformable film located between the contacts, the support 136 and thus, distal and proximal first contacts 130e, 131e are also moved translationally in the direction of the load F1. This causes the distal and proximal first contacts 130e, 131e, respectively, to come into electrical communication with the second (opposing) contact 150, closing switch 126e, and activating directional acoustic transducer element 160a. Further, gap 142b is eliminated, and gap 142a approximately doubles. In this manner, the acoustical signal produced by the directable acoustic transducer assembly 120 is aimed toward the tissue causing the load (see bump 504). In an embodiment of the invention, if the tip 180 comes into contact with the tissue wall 502 while the catheter body 110 does not come into contact with the tissue wall 502, the tip 180 may be at least partially bent. The invention may be configured for switch closure via bending of the tip 180 relative to the catheter body 110 in an embodiment of the invention. Mounting of the contacts 130a-130h, 131a-131h, 150 on an elastic foundation, for example elastic foundation 136$_{EF}$, may allow more forceful tip contact to result in activation and/or operation of more transducers 160a-160h progressively. Mounting the contacts 130a-130h, 131a-131h, 150 on an elastic foundation 136$_{EF}$ also has the advantage that contact damage can be prevented due to compressive overloading. In a typical application, the tip 180, not the catheter body 110, will primarily be in contact with the tissue. This means that the tip 180 will have an activating torque applied to it.

It will be appreciated that regardless of the design details, one set of contacts 130a-130h, 131a-131h on one substrate 136 can easily be arranged to be movable or deflectable (e.g., radially and/or axially) relative to a second set of mating contacts 150 on a second opposed or nearby substrate. In a preferred approach, the two contact bearing substrates comprise a switch ring subassembly, in which two opposed substrates are mechanically connected to each other with a deformable elastomer, wherein the elastomer does not interfere with opposed contact closure itself, but does otherwise flexibly join the rings. This approach allows for the contact ring subassembly to be provided as a pretested module (sandwich) in manufacturing. In accordance with an embodiment of the invention, the inventive circumferential or circular switch array 126, including a switch ring subassembly as described herein, may be used to selectively activate a transducer 160 in a desirable direction due to a specific load (e.g., a load that causes tip bending or tip axial compression).

FIG. 2A depicts another example of a self-directed acoustic transducer assembly 220 (shown without an overlying acoustic lens) implemented in a MID 200. The configuration shown in this FIG. 2A is similar to that shown in FIG. 1A, with the primary exception being that the distal first contacts 230a, 230b, 230c, 230d, 230e, 230f, 230g, 230h (230b, 230c, 230d, 230f, 230g are not visible) are connected to the directional acoustic transducer elements 260a, 260b, 260c, 260d, 260e, 260f, 260g (260g is not visible), and the second contact 250 is connected to the outer surface 151 of the support 236. Accordingly, one contact may be connected with the directional acoustic transducer element, and another contact may connected with a support. The basic manner in which the self-directed acoustic transducer assembly 220 operates is substantially the same as that of the self-directed acoustic transducer assembly 120.

The tip 280 of the MID 200 may be connected with the directable acoustic transducer assembly 220 by fixedly connecting, such as by bonding, the outer surface 284 of the boss 282 with the inner surface 238 of the support 236. The body 210 of the MIB 200 may also be fixedly connected with the support 236. The tip 280 may be connected with the directable acoustic transducer assembly 220 to create a subassembly that may then be connected with the body 210.

In this depicted example, the self-directed acoustic transducer assembly 220 includes eight directional acoustic transducer elements 260a-260h (260h not visible), each with a width 274 along the tip axis of about 1 mm, a circumferential diameter of about 2 to 3 mm and separated by an indentation or slot 244 with a width 246 on the circumferential surface of about 15-40 microns. This slot width 246 is consistent with readily available and known laser dicing or abrasive microblade dicing. The diameter is consistent with conventional popularly sized catheters used today which are in the 2.0-3.5 mm diameter range. The transducer width of 1 mm is large enough to attain reasonable signal-to-noise performance and manufacturability, yet small enough that it does not create an overall tip region which has too long of an inflexible length. The directional acoustic transducer elements 260a-260h (260h not visible) are formed in a transducer ring 228. For example and as generally depicted in FIG. 2B, directional acoustic transducer element 260c includes a first electrode 290c, piezoelectric material 294c, second electrode 292c and a matching layer 296 and is integrated with the backing layer 237.

Figure 3A:
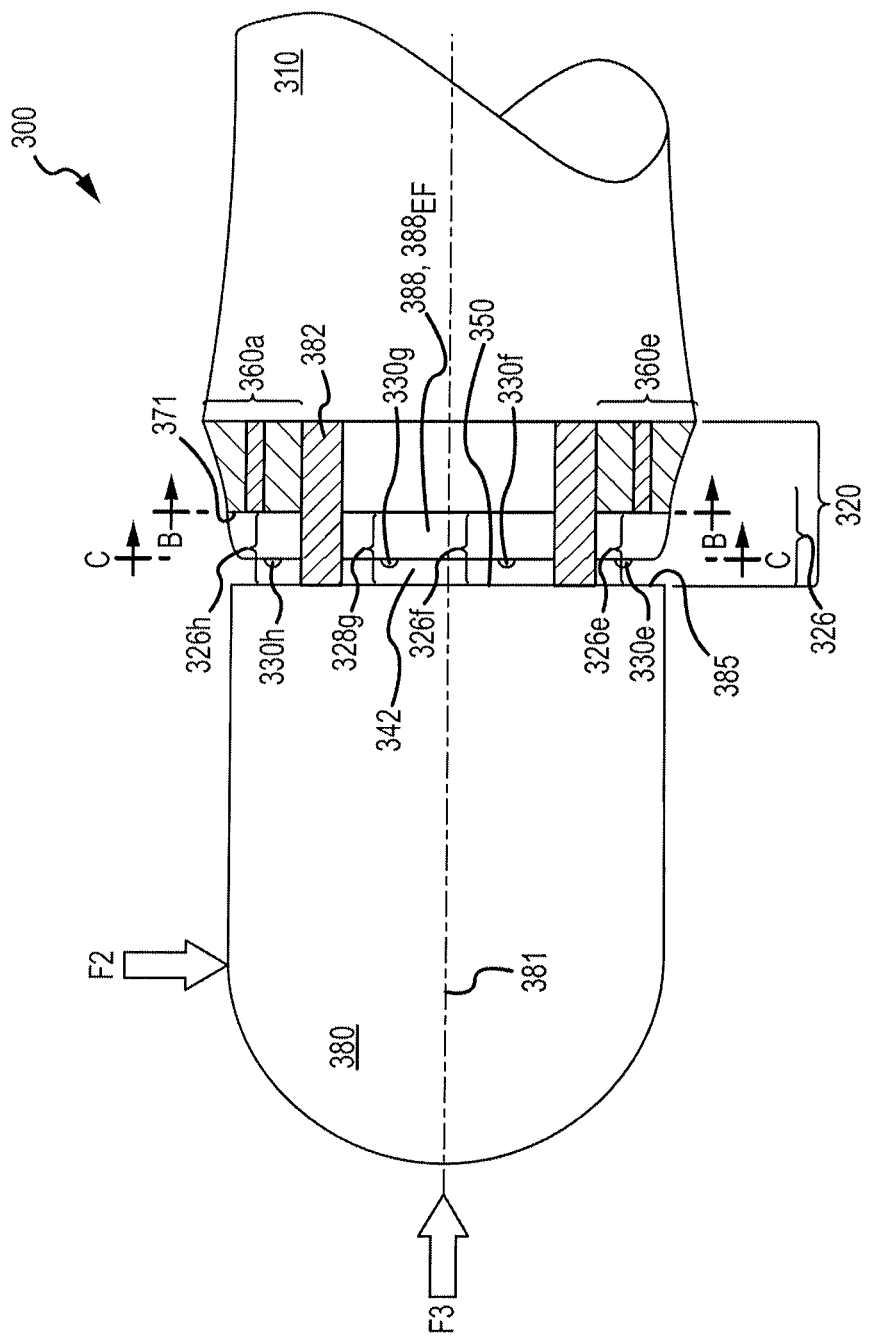
FIG. 3A depicts a partial cross-sectional view of another embodiment of a directable acoustic transducer assembly implemented with a medical insertion device.

Another example of a directable acoustic transducer assembly 320 implemented in a MID 300 is shown in FIGS. 3A-3C. The directable acoustic transducer assembly 320 is, for exemplary purposes, implemented within a catheter that includes a body 310 and a tip 380 with a boss 382. As shown in FIG. 3A, the directional acoustic transducer 360 may be connected with the boss 382. In general, the directable acoustic transducer assembly 320 includes a switch array 326 and a directional acoustic transducer 360. The directional acoustic transducer 360 includes a plurality of directional acoustic transducer elements 360a-360h, each of which include a transducer 328a-328h, backing layer 337, and a lens 340. The transducers 328a-328h may be formed in a common transducer ring 328 or separately. The transducers 328a-328h may comprise any type of transducer, including for example, but not limited to, forward looking transducers.

As shown in FIG. 3A, the switch array 326 includes a plurality of switches (e.g., contact pairs) 326e, 326f, 326g, 326h (switches 326a, 326b, 326c, 326d not shown). Each of the switches 326a-326h includes one or more first contacts and a second contact. In accordance with an embodiment of the invention, the second contact may be a shared common contact. In the present example, each switch 326a-326h includes first contacts 330a, 330b, 330c, 330d, 3303, 330f, 330g, 330h, respectively, and a second shared contact 350 separated by a nominal (e.g., zero tip load state) gap 342. As the tip 380 is generally metallic, the body-facing end 385 of the tip 380 may even serve as the shared second contact 350 or may be plated with an electrical conductor to serve as such. The plurality of first contacts 330a-330h are connected with the tip-facing end 371 of the directional acoustic transducer 360 via an electrically insulating material 388 such as, alumina, glass, polyimide or pc-board material. The insulating material 388 may cover all or part of the tip-facing end 371 of the directional acoustic transducer 360 and/or may form a ring 385 around the boss 382, as shown in FIG. 3C. In FIG. 3C the ring 385 is adjacent the boss 382. However, the ring 385 may be separated from the boss 382. Further, the gap 342 may be filled with a compressible, preferably hydrophobic material such as, a ePTFE film, to prevent fluids such as, blood or water, from penetrating into the gap 342; however, it would be arranged not to prevent and/or block the act of electrical contact-to-contact closure.

There is preferably at least one switch 326a-326h associated with each directional acoustic transducer element 360a-360h. Generally, this means that there is at least one first contact for each directional acoustic transducer element 360a-360h. However, more first contacts per transducer element 360a-360h may be included to increase the angular sensitivity of the directable acoustic transducer assembly 320. In the example shown in FIGS. 3A-3C, the directable acoustic transducer assembly 320 includes eight switches 326a-326h (each with one first contact 328a-328h, respectively), eight directional acoustic transducer elements 360a-360h and a common shared second contact 392. The second contact(s) may comprise a single common larger electrode in many cases. However, the number of these elements shown is for exemplary purposes only and almost any number of switches, contacts, and directional acoustic transducer elements may be included. In an embodiment, the contacts 328a-328h, 392 may include an elastic foundation (such as elastic foundation $388_{EF}$, FIG. 3A). An elastic foundation may be useful as it may prevent overloading of any particular contact and subsequent physical crushing of the contact which would change its switching behavior, contact-resistance, or reliability. An elastic foundation for one of the contact sets (e.g., 328a-328h and 392) may allow modification to the manner in which the contacts may close at a given tip-bending angle.

The switches 326a-326h are placed in communication with the directional acoustic transducer elements 360a-360h (by, for example, electrical wires, traces, or other electrical interconnects), so that when an angulating load is placed on the tip 381 of the MID 300, for example, by tissue, one or more of the switches, such as switch 328e, on the side of the MID 300 generally opposite that of the load F2 activate (e.g., fire) or enable (e.g., close the connection to allow firing) the directional acoustic transducer element 360a that faces the tissue causing the load F2. The passive receive function of that transducer element 360a may also be enabled. Thus, the self-directable acoustic transducer assembly 320 is able to sense the direction of the load F2 (e.g., because of the wiring arrangement of the switch/transducer interconnections) and activate the directional acoustic transducer element 360a facing the load F2. In other words, the directable acoustic transducer assembly 320 is essentially self-aiming or self-directed.

The switches 326a-326h may alternately or additionally be placed in communication with the directional acoustic transducer elements 360a-360h so that when a load F3 with a direction along the longitudinal axis 381 of the tip 380 is placed on the tip 380, the switches 326a-326h activate all the directional acoustic transducer elements 360a-360h indicating the direction of the load F3. Thus, the directable acoustic transducer assembly 320 is able to identify the direction of the load F3.

Figure 6A:
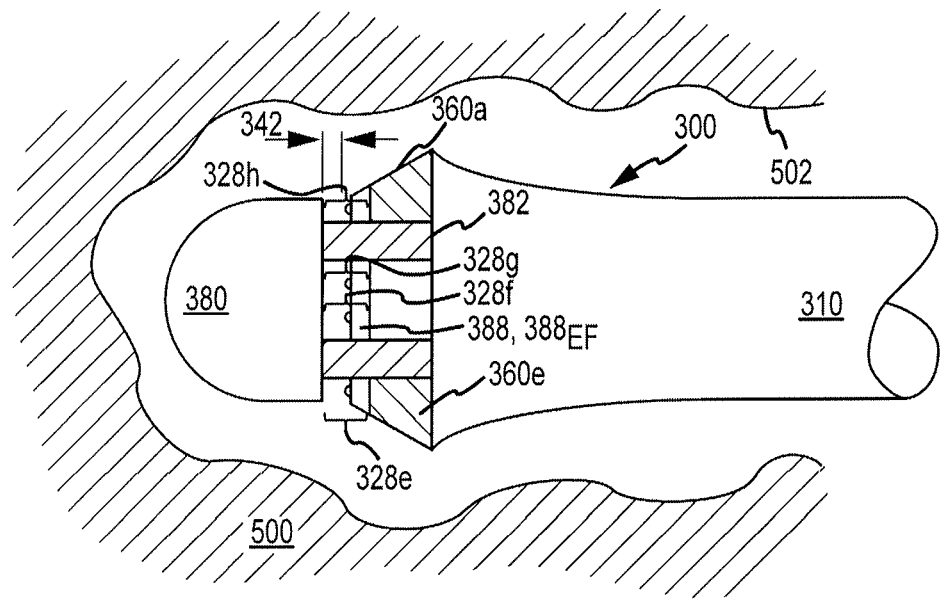
FIG. 6A depicts a partial cross-sectional view of the directable acoustic transducer assembly implemented with the medical insertion device of FIG. 3 inserted into tissue that applies a longitudinal load to the assembly.
Figure 6B:
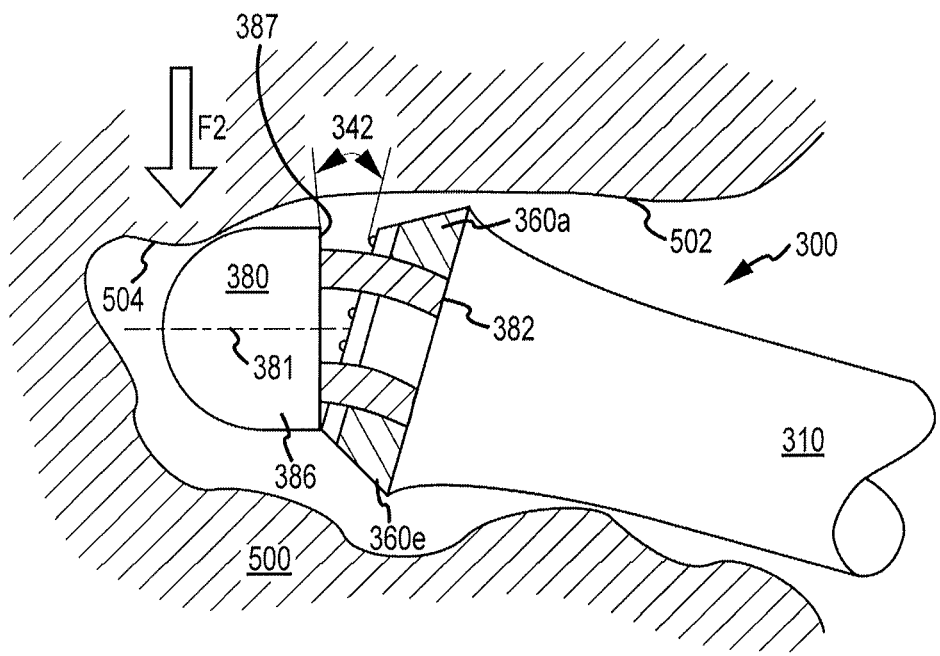
FIG. 6B depicts a partial cross-sectional view of the directable acoustic transducer assembly implemented with the medical insertion device of FIG. 3 inserted into tissue.

An example of the way in which a tip-angulating tissue load activates the self-directed acoustic transducer assembly 320 is shown in FIGS. 6A and 6B. In FIG. 6A, the MID 300 has been inserted into tissue 500 but does not contact the tissue wall 502. The tip 380 and boss 382 are generally coaxial with the directionable acoustic transducer assembly 320. The gap 342 between the second contact 392 and plurality of first contacts 326a-326h is about consistent. In addition, the switches 326a, 326b, 326c, 326d, 326e, 326f, 326h are placed in communication with the opposing directional acoustic transducer elements 360e, 360f, 360g, 360h, 360a, 360b, 360c, 360d, respectively, via electrical wires or other electrical interconnects. Thus, switch 326e is in communication with directional acoustic transducer element 360a so that when switch 326e closes, a transmit voltage may be usefully applied across the contacts of directional acoustic transducer element 360a thus, activating directional acoustic transducer element 360a. The same switch allows echo-signal reception thereafter.

In FIG. 6B, load F2 is placed on the tip 380 of the MID 300 in a direction approximately parallel to the longitudinal axis 381 of the tip 380. In this example, load F2 is imposed when the tip 380 encounters a bump 504 in the wall 502 of the tissue 500. The load F2 causes the portion 387 of tip 380 closest to the tissue causing the load 504 to move in an angular manner (rotate) relative to the remainder of the MID 300 in a direction away from directional acoustic transducer element 360a. Due to the load F3, the flexibility of the boss 382 and the compressibility of the ePTFE film located between the contacts, the switch 328e is closed thus, activating directional acoustic transducer element 360a. In addition, the gap 342 of switch 328e goes approximately to zero and the gap 342 of switch 328h angularly increases. In this manner, the acoustical signal produced by and/or received by the directable acoustic transducer assembly 320 is aimed and/or oriented toward the tissue causing the load.

In any of the various embodiments, the invention comprises a tip 180, 280, 380, 480 having at least one transducer 160, 260, 360, 460 activated by a tip force and looking at tissue of interest when tissue contact causes the tip force. The most general implementation is a ring transducer array (e.g., 128, 228) switched by a ring contact array (e.g., 126, 326), wherein tip articulation turns on a subset of (one or more) transducer elements 160a, 260a, 360a, 460a facing the tissue. There are several ring contact array designs, wherein a ring of contacts can be locally squeezed shut and one or more elements may move with respect to one or more other elements. The elements may move in any number of various directions and/or orientations so long as the appropriate switch(es) and corresponding contact(s) close in the process. For example, at least part of the load may be in a direction that causes at least two mating contacts of the plurality of contacts to close their respective gap along a closure direction that is substantially along the longitudinal axis of the medical insertion device, along a closure direction that is substantially perpendicular to the longitudinal axis of the medical insertion device, and/or along a closure direction that is a combination of substantially along the longitudinal axis and substantially perpendicular to the longitudinal axis, in accordance with various embodiments of the invention. The closure of the contact(s) may thereby cause at least one directional acoustic transducer element facing the tissue causing the load to be activated, such that the tissue causing the load is in the field of view of the transducer element. In most cases, the mating contact pairs will be mounted upon cylindrical or flat opposed surfaces as generally shown herein. However, the invention allows for any contact array mounting surface shape including elastically deformable ones as described herein. The ring contact array may include a plurality of substrates or supports that may be generally cylindrical, disc-shaped, annular, or a combination thereof in accordance with various embodiments of the invention.

FIG. 6B shows an example of the way in which a longitudinal load activates the directable acoustic transducer assembly 320 and the ranges in the MID 300 and the directable acoustic transducer assembly 320 relative to relationships of the components in FIG. 3A.

Figure 6C:
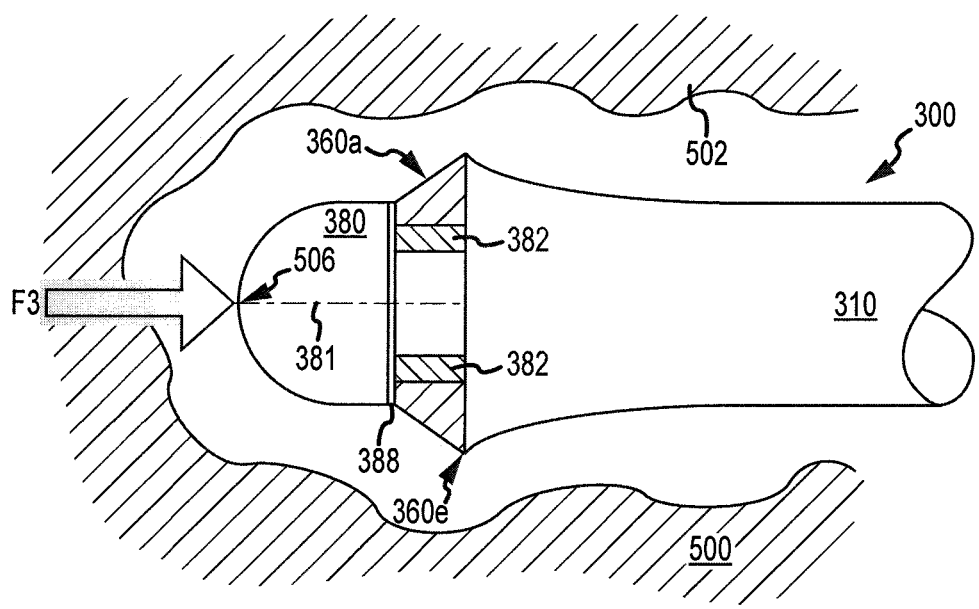
FIG. 6C depicts a partial cross-sectional view of the directable acoustic transducer assembly implemented with the medical insertion device of FIG. 3 inserted into tissue that applies a angulating load to the assembly.

In FIG. 6C, load F3 is placed on the tip 380 of the MID 300 along the longitudinal axis 381 of the tip 380 by a portion 506 of the wall 502 that is approximately along the longitudinal axis 381 of the tip 382. In this example, the load F3 (e.g., axial force) causes the tip 380 to move towards approximately all the directional acoustic transducer elements 328a-328h (see FIG. 3A) so that approximately all the switches 326a-326h (see FIG. 3A) close. Thus, approximately all the directional acoustic transducer elements 360a-360h are activated. This indicates the direction of the tissue 506 causing the load F3 is at the distal end of the tip 382. In this manner, the directable acoustic transducer assembly can also detect the direction of tissue 506 imposing a longitudinal load on the tip 382. In another embodiment (not shown), the tip 380 of the MID 300 may be configured to move (e.g., slide) sideway relative to the catheter body 310, which may cause the closure of one or more contacts on the switch array 326. In another embodiment (not shown), the tip 380 of the MID 300 may be configured to switch in response to rotational torques applied to various axes of the tip 380.

Figure 4A:
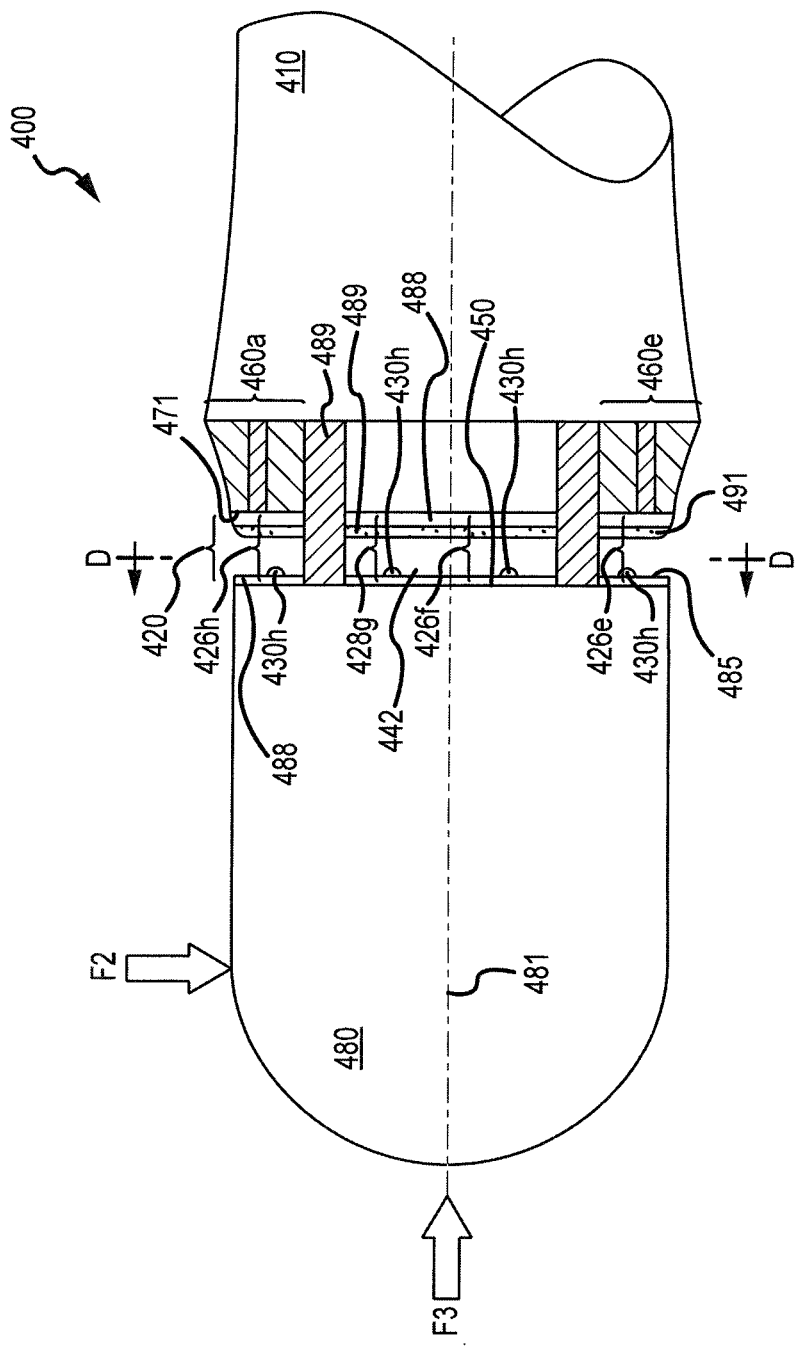
FIG. 4A depicts a partial cross-sectional view of yet another embodiment of a directable acoustic transducer assembly implemented with a medical insertion device.
Figure 4B:
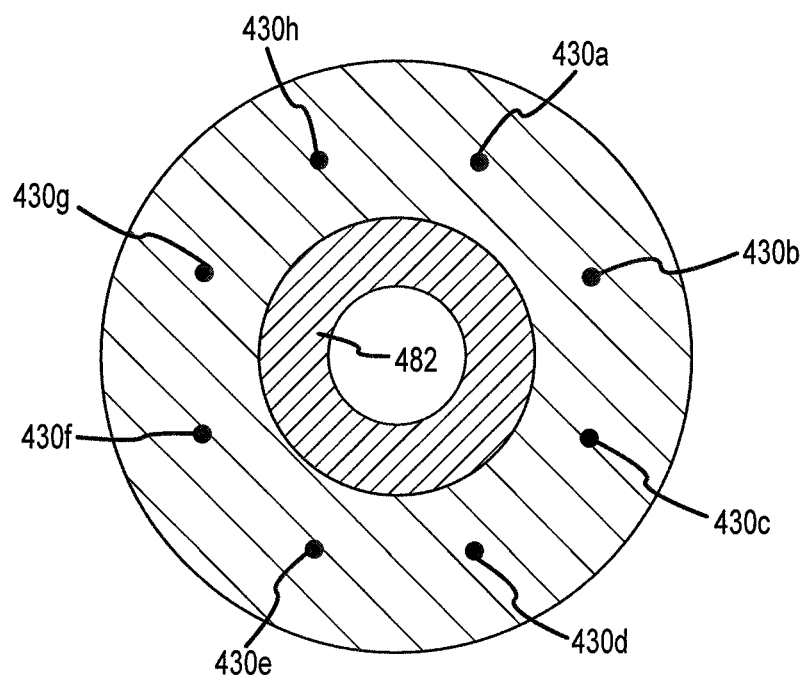
FIG. 4B depicts a cross-sectional view of the directable acoustic transducer assembly of FIG. 4A taken along line D-D.

FIGS. 4A-4B show another example of a directable acoustic transducer 420 implemented in a MID 400. The configuration and operation of the directable acoustic transducer assembly 420 is similar to that of FIGS. 3A-3C. However, in this embodiment, the separate contacts 430a-430h are connected with body-facing end 485 of the tip 480. The contacts 430a-430h are thus connected with a surface of a tip 480 of the MID 400 and/or with a first support connected with a surface of the tip 480 of the MID 400. The contacts 430a-423h may face the plurality of directional acoustic transducer elements 460a-460h. The second contact 491 is connected with the tip-facing end 471 of the directional acoustic transducer elements 460a-460h (only 460a and 460e are shown) via a first electrically insulating material 471 and/or via a second support connected with the directional acoustic transducer elements 460a-460h. The first contacts 430a-430h are connected with the body-facing surface of the tip 480. If the body-facing surface 485 of the tip 480 is electrically conductive, the separate contacts 430a-430h are connected with the body-facing surface 485 of the tip 480 via a second electrically insulating material 488.

In addition to activating directional acoustic transducer elements (e.g., 160a-160h, 260a-260h, 360a-360h, 460a-460h) in response to a specific directional load on an MID (e.g., 100, 200, 300, 400), it will be clear that when a subset of (e.g., one or more) transducer elements turn on, sufficient force has occurred to cause that amount of articulation or deformation. Accordingly, the bending force which causes transducer turn on can easily be bench calibrated during product design. The turn on event may thus be a helpful indication of a specific minimum tip force having been created and present against the tissue. In the case of the contacts of the switch array (e.g., 126, 326) mounted on an elastic foundation (e.g., elastic foundation 136$_{EF}$) and/or contacts of the switch array turning on sequentially with increasing force/articulation, it should be clear that this provides essentially a variable tip force reading to the user of the inventive MID.

Figure 7:
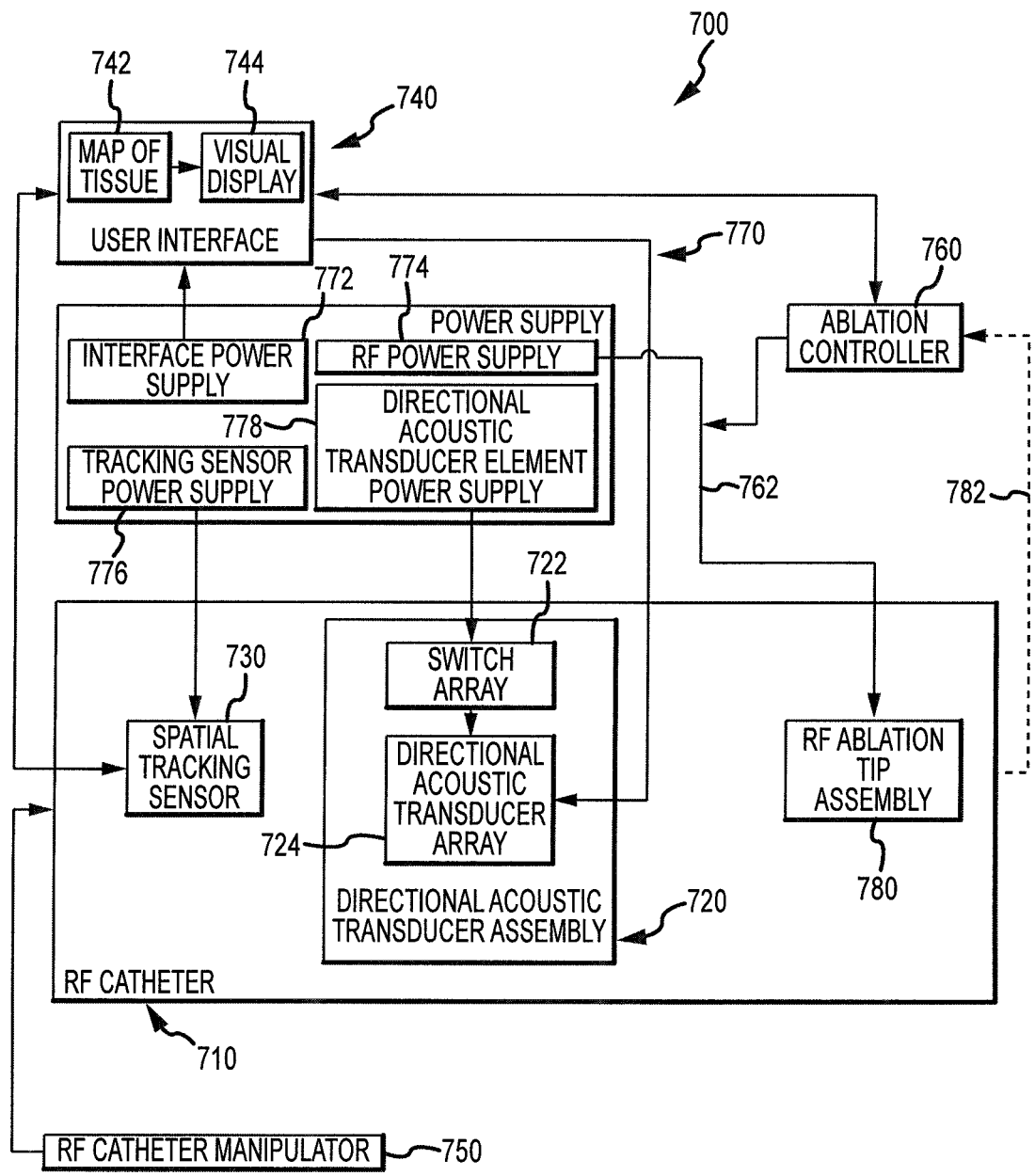
FIG. 7 generally illustrates a functional block diagram of an embodiment of an RF ablation system.

There are many applications and uses for which such an inventive acoustic transducer assembly or array (e.g., 120, 220, 320, 420) may be used. An example of one of these applications and uses is shown in FIG. 7. FIG. 7 is a functional block diagram of an RF ablation system 700. Such a system 700 may be used in applications in which heating tissue and/or forming thermal lesions with RF energy in tissue is involved. For example, to treat an arrhythmia of the heart, heart tissue containing the conductive paths responsible for the arrhythmia may be destroyed by heating and necrosing the affected area (the target tissue) using RF energy generated and applied by an RF ablation system, such as the system 700 shown in FIG. 7.

The RF ablation system 700 generally includes a flexible RF catheter 710, an RF catheter manipulator 750 such as a control handle (e.g., hand-driven lever(s) or knob(s) on a control handle) or robot, an ablation controller 760, and a user interface 740. The system 700 may also include a power supply 770. The RF catheter 710 preferably includes a spatial tracking sensor 730, the inventive self-directing transducer assembly 720, and an RF ablation tip assembly 780. The user interface 740, spatial tracking sensor 730, and RF catheter manipulator 750 are used to guide the catheter 710 within tissue. The user interface 740 may include a 2D or 3D image or computer-constructed map or model of the tissue 742 into or onto which the catheter 710 will be introduced. The map and/or image 742 may be communicated to a doctor and/or physiologist via a visual display 744, such as a computer monitor. The map or image is preferably updated over time, and may be updated frequently. When the catheter 710 is inserted into tissue, the spatial tracking sensor 730 determines the position and orientation of the catheter 710 within the tissue and communicates these values to the user interface 740 which likely includes a two dimensional (2D) or three dimensional (3D) tissue map or organ-model. The user interface 740 displays the position and orientation of the catheter 710 with respect to the map and/or image 742 via the visual display 744 (e.g., using known 3D spatial, tracking systems such as the Ensite™ System from St Jude Medical (electric field tracking) and/or the Carto™ system for Biosense-Webster (magnetic field tracking)). The catheter 710 is moved within the tissue by an RF catheter manipulator 750. Using the manipulator 750 to move the catheter 710 within the tissue may be a manual procedure. In other words, the doctor or physiologist moving the RF catheter uses the manipulator 750 to guide thecatheter 710 by hand, such as by watching such movements using fluoroscopy. As the catheter 710 is moved within the tissue by the RF catheter manipulator 750, the spatial tracking sensor 730 communicates the position and orientation of the catheter 710 to the user interface 740, which displays the changing position and orientation.

After the RF catheter 710 has been positioned within the anatomy to be proximate the target tissue, such as on a selected cardiac endocardial surface to be ablated, the directional acoustic transducer assembly 720 self-directs a beam of acoustic energy towards the forcefully contacting target tissue to obtain pinged acoustic information about the tissue. The term "forcefully" typically means a mechanical load of between about 5 and 100 grams, and more usually between 10 and 50 grams. Higher forces may cause perforation of heart tissues, whereas lower forces may not provide good enough RF ablative power coupling. The directional acoustic transducer assembly 720 includes a contact switch array 722 and directional acoustic transducer elements 724 wired thereto.

As described previously, the self-directed acoustic transducer assembly 720 includes switches within the switch array 722, a subset of which respond by electrically closing in response to a load imposed on the self-directed acoustic transducer assembly 720 and/or the tip of the RF catheter 710 by the target tissue. The switches responding to the load activate the tissue facing directional acoustic transducer element(s) 724. The activated acoustic transducer elements 724 transmit an acoustic signal towards the target tissue and subsequently receive acoustic echoes therefrom. From the acoustic signals or echoes reflected by the target tissue and received by the activated acoustic transducer element(s), information can be obtained about the target tissue and/or whether the lesioning is in progress or completed. For example, the thickness of the target tissue or a state of a lesion may be determined by the state of a thermally induced microbubble cloud.

The RF ablation tip assembly 780 and the ablation controller 760 are used to provide a therapeutic ablative treatment to the tissue. In the present example, the ablation controller 760 is in communication with the RF power supply line 762 that couples the RF power supply 774 to the RF ablation tip assembly 780. The ablation controller 760 is in communication with the RF power supply 774 and the RF ablation tip assembly 780 via the RF power supply line 762.

The ablation controller 760 controls the operation of the RF ablation tip assembly 780 in part by controlling the RF power supplied to the tip assembly 780. It preferably controls the strength and duration of the RF energy applied to the tissue by the RF ablation tip assembly 780 as input by the physician orpractitioner. The ablation controller 760 may optionally be configured to receive pinging feedback from the RF ablation tip assembly 780 in accordance with an embodiment of the invention that has an automatic feedback loop via line 782. Some embodiments of the invention may also utilize a return current patch placed externally on a patient's body as is known to those of ordinary skill in the art.

The RF ablation tip assembly 780 provides ablative heating RF energy to tissue that needs to be treated. The RF ablation tip assembly 780, when activated to ablate, ablates any tissue surface it touches, thereby resulting in generally hemispherical lesions having their center underlying the catheter tip. In general, the RF ablation tip assembly 780 typically includes an irrigated single bipolar RF ablation electrode. Thus, the RF energy it produces is non-directional. When the ablation controller 760 activates the tip assembly 780 and the tip assembly 780 is in contact with tissue, the tip assembly 780 creates a lesion going into the tissue that is approximately hemispherical or mushroom shaped. The favorable electrical impedance matching of the ablative RF tip to the tissue causes RF induced ablation preferentially in the tissue and not in the otherwise-surrounding bloodpool in the known manner.

Before, during and after the ablation has been performed, the self-directed acoustic transducer assembly 720 may be used to gather information regarding the target tissue and the lesion produced by the RF ablation tip assembly 780. Information about tissue thickness and closeness of anatomic features (such as the esophagus or aorta) to be thermally protected may also be gathered. As previously described, the transducer assembly 720 can measure the thickness of the target and nearby tissues which are arranged to be in the acoustic beam path. The gathered information may include determining the depth, volume or continuity of one or more lesions produced in the target tissue. Because the lesion is typically approximately hemispherical, the measured depth of the lesion may be used to calculate the width of the lesion (the width being approximately twice the depth).

The RF ablation system 700 may also include a power supply 770. The power supply may include an interface power supply 772, an RF power supply 774, a tracking sensor power supply 776 and an acoustic transducer power supply 778. These supplies 772, 774, 776, 778 provide the type and amount of power required by the user interface 740, RF ablation tip assembly 780, spatial tracking sensor 730, and directional acoustic transducer assembly 720, respectively.Although, the interface power supply 772, RF power supply 774, tracking sensor power supply 776 and acoustic transducer power supply 778 are shown as included in a single power supply 720, they may be implemented separately or in any combination. They may be included within the component to which they supply the power. One or more of these might be replaced with a battery or fuel cell.

Although a finite number of embodiments of this invention have been described above with a certain degree of particularity, those skilled in the art could make numerous alterations to the disclosed embodiments without departing from the spirit or scope of this invention. For example, the number of switches in the switching array and the number of directional acoustic transducer elements may be higher or lower than those described in the disclosure. For another example, a user of the inventive assembly may sequentially sample scanlines or directions along multiple adjacent directions toward the tissue such that the user may get information over an angular range. The sequential sampling may be done by closing the contacts to a plurality (e.g., five) transducers facing tissue, and then selectively pulsing the transducers from the supporting console separately or with fixed phase delays relative to each other. The set of pinged scanlines or directions may essentially be a simplistic narrow angle sector ultrasonic image. An important feature of this invention is the use of a selectively self-activating directed acoustic transducer assembly instead of an omnidirectional acoustic transducer in MIDS. For example, the self-activating directed (therefore self-directed) acoustic transducer assembly uses a switch array to activate directional acoustic transducer elements for which the target tissue is in their field of view. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims

What is claimed is:
1. An acoustic transducer assembly for use in a medical insertion device having an axis, the acoustic transducer assembly comprising:
a plurality of directional acoustic transducer elements circumferentially disposed about the axis, each acoustic transducer element being configured to transmit a respective acoustic beam in a predetermined direction, and receive a respective returning acoustic echo in a respective field of view; and
a switch array in communication with the plurality of directional acoustic transducer elements and configured to activate or enable at least one of the plurality of directional acoustic transducer elements in response to a load on a portion of the medical insertion device other than on the plurality of directional acoustic transducer elements, said switch array includes a plurality of switches in communication with the plurality of directional acoustic transducer elements, at least one of the plurality of switches including a first contact on a first support and a second contact on a second support wherein the first contact is separated from the second contact by a gap, and wherein at least one of the first and second supports comprises an elastic foundation having a surface on which one of the first contact and the second contact is situated, and which directly touches said one of the first contact and the second contact without an intervening structure, said elastic foundation being one of axially disposed and radially-inwardly disposed relative to said one of the first contact and the second contact.

2. The acoustic transducer assembly of claim 1, wherein the load on the medical insertion device is at least partially caused by contact with a target and wherein the at least one of the plurality of directional acoustic transducer elements is configured to aim an acoustic beam in a direction of the target causing the load when activated by the switch array.

3. The acoustic transducer assembly of claim 1, wherein the load on the medical insertion device is at least partially caused by bending or articulation of the medical insertion device and wherein the at least one of the plurality of directional acoustic transducer elements is configured to aim an acoustic beam in a respective predetermined direction when activated by the switch array.

4. The acoustic transducer assembly of claim 2, wherein the switch array is further configured so that a closing switch of the switch array is located diametrically opposite or on an opposed tip region from the tissue causing the load.

5. The acoustic transducer assembly of claim 2, wherein the switch array is further configured to activate at least one of the directional acoustic transducer elements closest to the target causing the load.

6. The acoustic transducer assembly of claim 2, wherein at least one directional acoustic transducer element for which the target causing the load is in said field of view and the at least one directional acoustic transducer element being activated by the switch array.

7. The acoustic transducer assembly of claim 2, wherein a subset of one or more of the plurality of switches activates at least one directional acoustic transducer element for which the tissue causing the load is in the field of view of the at least one directional acoustic transducer element.

8. The acoustic transducer assembly of claim 2, wherein the switch array includes a plurality of contacts configured so that closure of predetermined contact pairs of the plurality of contacts causes activation or enabling of corresponding predetermined transducers that face the tissue causing the load.

9. The acoustic transducer assembly of claim 7, wherein the plurality of switches includes a plurality of first contacts, the gap separating the first contacts and the second contact is substantially filled or sealed with a compressible hydrophobic material which is configured to still allow mating electrical contact closure.

10. The acoustic transducer assembly of claim 7, wherein the plurality of switches includes a plurality of contacts that are mounted upon at least one polygonal, cylindrical, or ring-shaped contact support.

11. The acoustic transducer assembly of claim 7, wherein the plurality of switches includes a plurality of contacts and wherein at least one of the plurality of contacts is mounted on a first support and at least one mating second contact of the plurality of contacts is mounted upon a second support, the first and second supports configured to have at least some of their mating contacts close when a predetermined load is applied to the medical insertion device.

12. The acoustic transducer assembly of claim 1, wherein at least one of the plurality of directional acoustic transducer elements includes an acoustic backing layer or one or more acoustic lenses or a combination thereof.

13. The acoustic transducer assembly of claim 12, wherein the one or more acoustic lenses steer one or more acoustic beams through at least one angle between 5 degrees and 60 degrees toward a tip of the medical insertion device and directs the one or more acoustic beams toward a target.

14. The acoustic transducer assembly of claim 1, wherein the plurality of directional acoustic transducer elements includes a plurality of transducers in a shape of a ring or cylinder.

15. The acoustic transducer assembly of claim 1, wherein each of the plurality of switches comprise a plurality of first contacts situated on the elastic foundation that form with the second contact respective contact pairs, wherein the number of contact pair closures correspond to a degree of articulation of a tip of the medical insertion device, the number of directional acoustic transducer elements activated by the switch array corresponds to the load on the medical insertion device, such that a greater load on the medical insertion device activates a greater number of directional acoustic transducer elements than a smaller load.

16. The acoustic transducer assembly of claim 1, wherein the directional acoustic transducer elements that are activated extend around less than 120 degrees of the circumference of the acoustic transducer assembly.

17. The acoustic transducer assembly of claim 16, wherein the directional acoustic transducer elements that are activated extend around 10 to 100 degrees of the circumference of the acoustic transducer assembly.

18. The acoustic transducer assembly of claim 1, wherein the medical insertion device comprises:
   a body; and
   a tip configured to bear the load and to bend or angularly articulate relative to the body,
   wherein the transducer assembly is connected with the body and the tip and wherein the switch array includes a plurality of the first contacts, and
   wherein the transducer assembly is configured to respond to a direction of a load on the medical insertion device and close at least one of the plurality of first contacts with respect to the second contact and aim a directional acoustic beam in the direction of a target creating the load.

19. The medical insertion device of claim 18, wherein the medical insertion device comprises one of an introducer, a catheter, a sheath, or a scope, or a combination thereof.

20. An ablation catheter system for performing a therapeutic procedure on a tissue portion, the ablation catheter system comprising:
   a user interface including a map, model or image of tissue into or onto which the ablation catheter is to be inserted;
   an ablation catheter having an axis and including:
      a spatial tracking sensor in communication with the user interface and configured to determine at least one spatial position or orientation parameter of the catheter relative to the map, model or image on the user interface;
      an acoustic transducer assembly that includes a plurality of directional acoustic transducer elements circumferentially disposed about the axis, each acoustic transducer element being configured to transmit a respective acoustic beam in a predetermined direction, and receive a respective returning acoustic echo in a respective field of view; and
   an ablation tip assembly adjacent to said acoustic transducer assembly and configured to apply ablation energy;
   a switch array in communication with the plurality of directional acoustic transducer elements and configured to activate or enable at least one of the plurality of directional acoustic transducer elements in response to a load on the ablation tip assembly, said switch array includes a plurality of switches in communication with the plurality of directional acoustic transducer elements, at least one of the plurality of switches including a first contact on a first support and a second contact on a second support wherein the first contact is separated from the second contact by a gap, and wherein at least one of the first and second supports comprises an elastic foundation having a surface on which one of the first contact and the second contact is situated, and which directly touches said one of the first contact and the second contact without an intervening structure, said elastic foundation being one of axially disposed and radially-inwardly disposed relative to said one of the first contact and the second contact; and an ablation controller in communication with the ablation tip assembly and configured to control the application of ablation energy by the ablation tip assembly.

21. The ablation catheter system of claim 20, wherein the ablation tip assembly is positioned distally of said acoustic transducer assembly.

\* \* \* \* \*